United States Patent [19]

Atwal et al.

[11] Patent Number: 4,855,301

[45] Date of Patent: Aug. 8, 1989

[54] 1,2,3,4-TETRAHYDRO-6-SUBSTITUTED-4-ARYL(OR HETEROCYCLO)-3-((SUBSTITUTED AMINO)CARBONYL)-2-THIOXO (OR OXO)-5-PYRIMIDINECARBOXYLIC ACIDS AND ESTERS

[75] Inventors: Karnail Atwal, Cranbury; George C. Rovnyak, Hopewell, both of N.J.

[73] Assignee: E. R. Squibb & Sons, Inc., Princeton, N.J.

[21] Appl. No.: 8,037

[22] Filed: Feb. 9, 1987

Related U.S. Application Data

[63] Continuation-in-part of Ser. No. 917,349, Oct. 9, 1986, abandoned, which is a continuation-in-part of Ser. No. 839,767, Mar. 14, 1986, abandoned.

[51] Int. Cl.[4] .................. A61K 31/505; C07D 239/36; C07D 401/06; C07D 403/06
[52] U.S. Cl. .................................... 514/269; 544/316; 544/123; 544/295; 544/58.6; 540/601; 514/212; 514/255; 514/227.8; 514/235.8
[58] Field of Search ............... 544/316, 318, 123, 295, 544/58.6; 514/274, 212, 255, 227.8, 235.8; 540/601

[56] References Cited

U.S. PATENT DOCUMENTS

| | | | |
|---|---|---|---|
| 4,532,248 | 7/1985 | Frankowick et al. | 514/302 |
| 4,609,494 | 9/1986 | Baldwin | 544/250 |
| 4,675,321 | 6/1987 | Baldwin et al. | 514/274 |
| 4,683,234 | 7/1987 | Cho et al. | 514/256 |
| 4,684,655 | 8/1987 | Atwal | 514/274 |
| 4,684,656 | 8/1987 | Atwal | 514/274 |
| 4,689,414 | 8/1987 | Atwal | 544/297 |
| 4,728,652 | 3/1988 | Atwal | 514/274 |
| 4,753,946 | 6/1988 | Atwal et al. | 514/274 |

FOREIGN PATENT DOCUMENTS

| | | | |
|---|---|---|---|
| 157219 | 10/1985 | European Pat. Off. | |
| 202654 | 11/1986 | European Pat. Off. | |
| 204317 | 12/1986 | European Pat. Off. | |
| 3234634 | 3/1984 | Fed. Rep. of Germany | 544/316 |
| 2501205 | 9/1982 | France | |
| 868030 | 5/1961 | United Kingdom | 544/316 |
| 84/1384 | 4/1984 | World Int. Prop. O. | |
| 84/1385 | 4/1984 | World Int. Prop. O. | |

OTHER PUBLICATIONS

Sweet et al, J. Amer. Chem. Soc., vol. 95, pp. 8741–8749, (1973).
McKinstry et al, Chemical Abstracts, vol. 38, entry 4318(4), (1944).
McKinstry et al, Chemical Abstracts, vol. 38, entry 2653(4), (1944).
Rutter et al, Chemical Abstracts, vol. 49, entry 14769i, (1955).
Khanina et al., Khim Farm Zh., vol. 12, pp. 1321–1322, (1978), "Synthesis and Pharmacological Investigation . . .".
Konyukhov et al.-Zh.Organ.Khim., vol. 1, No. 8, pp. 1487–1489, (1965), "Synthesis and Investigation . . . ".
Elkasaby, Pakistan J.Sci.Ind.Res., vol. 21, No. 2, pp. 58–61, (1978), "Condensation of Ethyl α-Acetylcinnametes with Thioureas".
George et al, Synthesis (1975), pp. 405–407, "Condensed Heterocycles from 5-Ethoxycarbonyl-6-methyltetrahydropyrimidin-2-ones".
Folkers et al., J.Am.Chem.Soc., vol. 56, pp. 1374–1377, (1938), "Researches on Pyrimidines . . . ".
J. Org. Chem., vol. 50, pp. 4227–4230, "Synthesis of Novel Dihydropyrimidines and Tetrahydropyrimidines", Cho et al.
Medicinal Chemistry, Burger Edit., 2nd Edit., 1960, pp. 565–571, 579–581, 600 and 601.

*Primary Examiner*—John M. Ford
*Attorney, Agent, or Firm*—Timothy J. Gaul

[57] ABSTRACT

Cardiovascular activity is exhibited by compounds having the formula

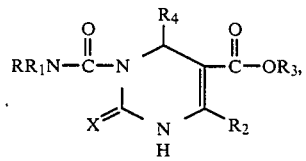

and pharmaceutically acceptable salts thereof wherein
X is oxygen or sulfur;
R is hydrogen, alkyl, cycloalkyl, aryl, or arylalkyl and $R_1$ is hydrogen, alkyl, cycloalkyl, aryl, heterocyclo,

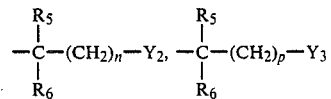

or halo substituted alkyl, or R and $R_1$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl or 1-pyrrolidinyl, 1-piperidinyl, or 1-azeipinyl substituted with alkyl, alkoxy, alkylthio, halo, trifluoromethyl or hydroxy;
$R_2$ is hydrogen, alkyl, alkenyl, alkynyl, cycloalkyl, aryl,

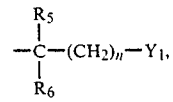

or halo substituted alkyl;
$R_3$ is hydrogen, alkyl, cycloalkyl, aryl, heterocyclo, (Abstract continued on next page.)

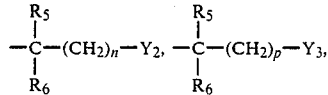

or halo substituted alkyl;
R₄ is aryl or heterocyclo;
R₅ and R₆ are each independently hydrogen, alkyl, —(CH₂)$_q$—aryl or —(CH₂)$_q$—cycloalkyl;
Y₁ is cycloalkyl, aryl, heterocyclo, hydroxyl, alkoxy, aryl—(CH₂)$_m$—O—, mercapto, alkylthio, aryl—(CH₂)$_m$—S—, amino, substituted amino, carbamoyl,

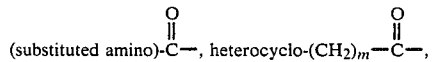

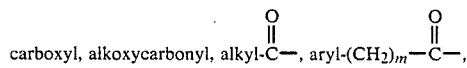

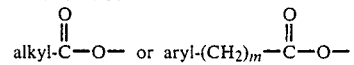

Y₂ is cycloalkyl, aryl, heterocyclo, carbamoyl,

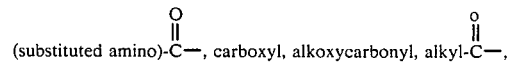

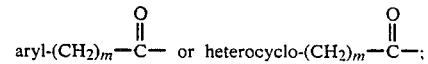

Y₃ is hydroxyl, alkoxy, aryl—(CH₂)$_m$—O—, mercapto, alkylthio, aryl—(CH₂)$_m$—S—,

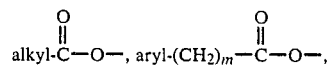

amino, or substituted amino;
q is 0, 1, 2 or 3;
m is 0 or an integer of 1 to 6;
n is 0 or an integer of 1 to 5; and
p is an integer of 1 to 5.

26 Claims, No Drawings

1,2,3,4-TETRAHYDRO-6-SUBSTITUTED-4-ARYL(OR HETEROCYCLO)-3-((SUBSTITUTED AMINO)CARBONYL)-2-THIOXO (OR OXO)-5-PYRIMIDINECARBOXYLIC ACIDS AND ESTERS

This is a continuation-in-part of U.S. patent application Ser. No. 917,349, filed Oct. 9, 1986, and now abandoned, which is a continuation-in-part of U.S. patent application Ser. No. 839,767, filed Mar. 14, 1986, and now abandoned.

BRIEF DESCRIPTION OF THE INVENTION

Compounds having the formula

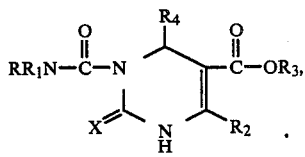

and pharmaceutically acceptable salts thereof, are cardiovascular agents. In formula I, and throughout the specification, the symbols are as defined below.

X is oxygen or sulfur;

R is hydrogen, alkyl, cycloalkyl, aryl, or arylalkyl and $R_1$ is hydrogen, alkyl, cycloalkyl, aryl, heterocyclo,

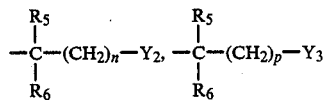

or halo substituted alkyl, or R and $R_1$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl or 1-pyrrolidinyl, 1-piperidinyl, or 1-azepinyl substituted with alkyl, alkoxy, alkylthio, halo, trifluoromethyl or hydroxy;

$R_2$ is hydrogen, alkyl, alkenyl, alkynyl, cycloalkyl, aryl,

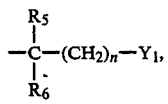

or halo substituted alkyl;

$R_3$ is hydrogen, alkyl, cycloalkyl, aryl, heterocyclo,

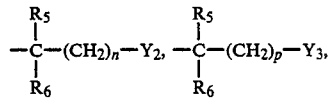

or halo substituted alkyl;

$R_4$ is aryl or heterocyclo;

$R_5$ and $R_6$ are each independently hydrogen, alkyl, —$(CH_2)_q$—aryl or —$(CH_2)_q$—cycloalkyl;

$Y_1$ is cycloalkyl, aryl, heterocyclo, hydroxyl, alkoxy, aryl—$(CH_2)_m$—O—, mercapto, alkylthio, aryl—$(CH_2)_m$—S—, amino, substituted amino, carbamoyl, (substituted amino)—C(O)—, heterocyclo—$(CH_2)_m$—C(O)—, carboxyl, alkoxycarbonyl, alkyl—C(O)—, aryl—$(CH_2)_m$—C(O)—, alkyl—C(O)—O— or aryl—$(CH_2)_m$—C(O)—O—;

$Y_2$ is cycloalkyl, aryl, heterocyclo, carbamoyl, (substituted amino)—C(O)—, carboxyl, alkoxycarbonyl, alkyl—C(O)—, aryl—$(CH_2)_m$—C(O)— or heterocyclo—$(CH_2)_m$—C(O)—;

$Y_3$ is hydroxyl, alkoxy, aryl—$(CH_2)_m$—O—, mercapto, alkylthio, aryl—$(CH_2)_m$—S—, alkyl—C(O)—O—, aryl—$(CH_2)_m$—C(O)—O—, amino, or substituted amino;

q is 0, 1, 2 or 3;

m is 0 or an integer of 1 to 6;

n is 0 or an integer of 1 to 5; and p is an integer of 1 to 5.

Listed below are definitions of various terms used to describe the compounds of this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 8 carbon atoms are preferred.

The term "halo substituted alkyl" refers to alkyl groups (as described above) in which one or more hydrogens have been replaced by chloro, bromo or fluoro groups. Exemplary groups are trifluoromethyl, which is preferred, pentafluoroethyl, 2,2,2-trichloroethyl, chloromethyl, bromomethyl, etc.

The term "aryl" refers to phenyl and substituted phenyl. Exemplary substituted phenyl groups are phenyl groups substituted with one, two or three alkyl, alkoxy, alkylthio, halo, nitro, cyano, hydroxy, amino, alkylamino, dialkylamino, trifluoromethyl, isothiocyanato, isocyanato, or difluoromethoxy groups.

The terms "alkenyl" and "alkynyl" refer to both straight and branched chain groups. Those groups having 2 to 8 carbon atoms are preferred.

The term "cycloalkyl" refers to those groups having 3, 4, 5, 6 or 7 carbon atoms.

The term "halo" refers to chloro, bromo, fluoro and iodo.

The term "heterocyclo" refers to fully saturated or unsaturated rings of 5 or 6 atoms containing one or two oxygen or sulfur atoms and/or one to four nitrogen atoms provided that the total number of hetero atoms in the ring is 4 or less. The heterocyclo ring is attached by way of an available carbon atom. Preferred monocyclic heterocyclo groups include 2- and 3-thienyl, 2- and 3-furyl, 2- and 3-pyrrolyl, 2-, 3- and 4-pyridyl, 2-, 4- and 5-imidazolyl, 2- and 3-pyrrolidinyl, 2-, 3- and 4-piperidinyl, and 2-, 3- and 4-azepinyl. The term heterocyclo also includes bicyclic rings wherein the five or six membered ring containing oxygen, sulfur and nitrogen atoms as defined above is fused to a benzene ring and the bicyclic ring is attached by way of an available carbon atom in the benzene ring. Preferred bicyclic heterocyclo groups include 4, 5, 6 or 7-indolyl, 4, 5, 6 or 7-isoindolyl, 5, 6, 7 or 8-quinolinyl, 5, 6, 7 or 8-isoquinolinyl, 4, 5, 6 or 7-benzothiazolyl, 4, 5, 6 or 7-benzoxazolyl, 4, 5, 6 or 7-benzimidazolyl, 4, 5, 6 or 7-benzoxadiazolyl, and 4, 5, 6 or 7-benzofurazanyl.

The term heterocyclo also includes such monocyclic and bicyclic rings as defined above substituted with one, or more, alkyl, arylalkyl, diarylalkyl, alkylthio, alkoxy, halo, nitro, oxo, cyano, hydroxy, amino, alkylamino, dialkylamino, trifluoromethyl, isocyanato, isothiocyanato or difluoromethoxy groups.

The term "substituted amino" refers to a group of the formula $-NZ_1Z_2$ wherein $Z_1$ is hydrogen, alkyl, or aryl—$(CH_2)_m$— and $Z_2$ is alkyl or aryl—$(CH_2)_m$— or $Z_1$ and $Z_2$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, or 1-pyrrolidinyl, 1-piperidinyl, or 1-azepinyl substituted with alkyl, alkoxy, alkylthio, halo, trifluoromethyl or hydroxy.

Those compounds of formula I wherein $R_4$ is heterocyclo, phenyl, or phenyl substituted with one, two or three alkyl, halo, nitro, cyano, amino, dialkylamino, trifluoromethyl, isothiocyanato or isocyanato groups are novel chemical compounds and as such form an integral part of this invention.

DETAILED DESCRIPTION OF THE INVENTION

The compounds of formula I, and the pharmaceutically acceptable salts thereof, are cardiovascular agents. They act as calcium entry blocking vasodilators and are especially useful as antihypertensive agents. Thus, by the administration of a composition containing one (or a combination) of the compounds of this invention, the blood pressure of a hypertensive mammalian (e.g., human) host is reduced. A single dose, or two to four divided daily doses, provided on a basis of about 0.1 to 100 milligrams per kilogram of body weight per day, preferably from about 1 to about 50 milligrams per kilogram per day, is appropriate to reduce blood pressure. The substance is preferably administered orally, but parenteral routes such as the subcutaneous, intramuscular or intravenous routes can also be employed.

It is believed that the compounds of this invention, in addition to being useful as hypotensive agents, may also be useful as anti-arrhythmic agents, anti-anginal agents, anti-ischemic agents, anti-fibrillatory agents, anti-asthmatic agents, and in limiting myocardial infarction.

The compounds of this invention can also be formulated for use as hypotensive agents in combination with a diuretic, or a beta-adrenergic agent, or angiotensin converting enzyme inhibitor. Suitable diuretics include the thiazide diuretics such as hydrochlorothiazide and bendroflumethiazide, suitable beta-adrenergic agents include nadolol, and suitable angiotensin converting enzyme inhibitors include captopril.

The compounds of formula I can be formulated for use in the reduction of blood pressure in compositions such as tablets, capsules or elixirs for oral administration, or in sterile solutions or suspensions for parenteral administration. About 10 to 500 milligrams of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The compounds of formula I wherein X is sulfur can be prepared by reacting a keto ester compound having the formula

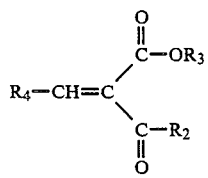

II with an S-(phenylmethyl)thiopseudourea having the formula

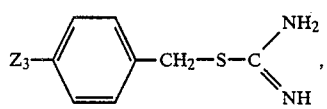

III or a salt thereof. In formula III, and throughout the specification, $Z_3$ is hydrogen or methoxy. The reaction mixture is heated in the presence of sodium acetate to yield a tautomeric mixture of compounds having the formulas

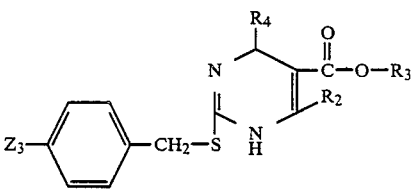

IV

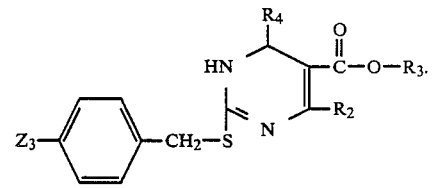

Reaction of a tautomeric mixture of formula IV with phosgene in the presence of an organic base followed by reaction with an amine having the formula $RR_1NH$  V, provided that neither R nor $R_1$ is hydrogen, yields the corresponding compound having the formula

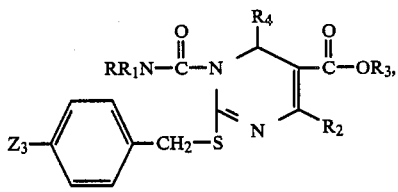  VI wherein neither R nor $R_1$ is hydrogen.

Those compounds of formula VI wherein one, or both, of R and $R_1$ is hydrogen can be prepared by reaction of a tautomeric mixture of formula IV with an isocyanate having the formula $$R_1-N=C=O.\qquad \text{VII}$$

A compound of formula VI wherein $Z_3$ is hydrogen can be converted to the corresponding product of formula I wherein X is sulfur by treatment with bromotrimethylsilane. A compound of formula VI wherein $Z_3$ is methoxy can be converted to the corresponding product of formula I wherein X is sulfur by treatment with trifluoroacetic acid and ethanethiol.

Compounds of formula IV may be prepared in nonracemic form by the reaction of a compound of formula IV with phosgene and a nonracemic alcohol (R*-OH) to obtain a compound having the formula

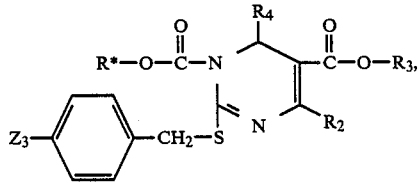  VIII wherein R* is the residue of a chiral alcohol.

Treatment of a compound of formula VIII with bromotrimethylsilane (when $Z_3$ is hydrogen) or with trifluoroacetic acid and ethanethiol (when $Z_3$ is methoxy) yields the corresponding compound having the formula

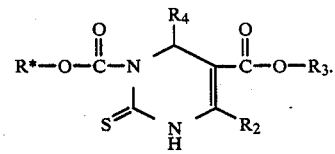  IX

The diastereomers of the compounds of formula VIII and IX can be separated by crystallization or chromatography.

Treatment of the purified diastereomers of a compound of formula IX with sodium methoxide, followed by p-methoxybenzyl chloride gives the corresponding compound of formula IV in nonracemic form, and these nonracemic compounds can be reacted as described above to obtain nonracemic products of formula I wherein X is sulfur.

The compounds of formula I wherein X is oxygen can be prepared by heating a keto ester of formula II with O-methylpseudourea

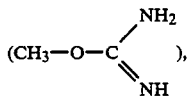

or a salt thereof, in the presence of sodium acetate or sodium bicarbonate to yield a tautomeric mixture of compounds having the formulas

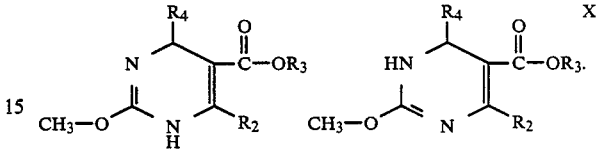  X

Reaction of a tautomeric mixture of formula X with phosgene in the presence of an organic base followed by reaction with an amine of formula V (R and $R_1$ have their broadest meanings) yields the corresponding compound having the formula

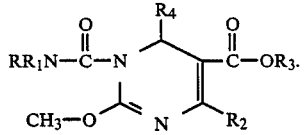  XI

Alternatively, those compounds of formula XI wherein R is hydrogen can be prepared by reaction of a tautomeric mixture of formula X with an isocyanate of formula VII.

A compound of formula XI can be converted to the corresponding product of formula I wherein X is oxygen by treatment with hydrochloric acid.

Alternatively, a tautomeric mixture of formula X can be reacted with p-nitrophenylchloroformate in the presence of an organic base to yield a compound having the formula

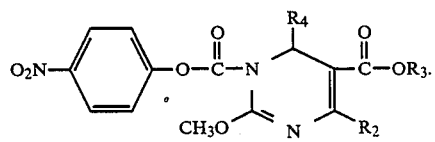  XII

Treatment of a compound of formula XII with an acid, followed by reaction with an amine of formula V (R and $R_1$ have their broadest meanings) yields the corresponding product of formula I.

The nonracemic form of a compound of formula I wherein X is oxygen can be prepared by forming a diastereomeric mixture of a compound of formula XI using an optically active amine (e.g., methylbenzyl amine). The diastereomers can be separated using conventional techniques such as chromatography and crystallization. The resolved diastereomers can be converted into the nonracemic form of a compound of formula X by treatment with sodium methoxide. The nonracemic form of a compound of formula X can be used to prepare the corresponding nonracemic form of a product of formula I via the nonracemic form of an intermediate of formula XI.

Alternatively, for those products of formula I wherein X is oxygen and R and $R_1$ are derived from optically active amines, the diastereomers of formula XI can be converted to products of formula I and the optically active products can be separated by chromatography or crystallization.

Alternatively, the nonracemic form of a product of formula I wherein X is oxygen can be prepared by first converting nonracemic compound of formula IV into the corresponding nonracemic compound of formula VI using the procedures described above. A nonracemic compound of formula VI can be reacted with an oxidizing agent (e.g., m-chloroperbenzoic acid) to yield a nonracemic product of formula I wherein X is oxygen.

An alternative procedure for preparing the nonracemic form of a product of formula I wherein X is oxygen and R and $R_1$ are each hydrogen comprises reacting the corresponding nonracemic product of formula I wherein $R_1$ is hydrogen and R is 1-phenylethyl with hydrogen bromide and acetic acid, or with trifluoroacetic acid.

Those products of formula I (including resolved enantiomers thereof) wherein X is sulfur can alternatively be prepared by first converting a methoxy containing intermediate of formula X (racemic or nonracemic) to the corresponding thio intermediate (racemic or nonracemic) of formula IV and then proceeding as described above.

In those instances wherein the reactants described above contain reactive substituents not meant to participate in the reaction, it may be necessary to first protect these functional groups, carry out the desired reaction, and then remove the protecting group.

The compounds of formula I that contain a basic or acidic group form acid addition and basic salts with a variety of inorganic and organic acids and bases. The pharmaceutically acceptable salts are preferred, although other salts may also be useful in isolating or purifying the product. Such pharmaceutically acceptable acid addition salts include those formed with hydrochloric acid, methanesulfonic acid, toluenesulfonic acid, sulfuric acid, acetic acid, maleic acid, etc. Pharmaceutically acceptable basic salts include alkali metal salts (e.g., sodium, potassium and lithium) and alkaline earth metal salts (e.g., calcium and magnesium). The salts can be obtained by reacting the product with an equivalent amount of the acid in a medium in which the salt precipitates.

Preferred compounds of this invention are those wherein:

$R_2$ is alkyl (especially methyl), $R_3$ is alkyl (especially isopropyl) and $R_4$ is 3-nitrophenyl, and R and $R_1$ are each hydrogen or one of R and $R_1$ is hydrogen and the other is (S)-1-phenylethyl.

The following examples are specific embodiments of this invention.

EXAMPLE 1

3-[(Ethylamino)carbonyl]-1,2,3,4-tetrahydro-6-methyl-4-(3-nitrophenyl)-2-thioxo-5-pyrimidinecarboxylic acid, methyl ester (A) S-(4-Methoxybenzyl)thiopseudourea, hydrochloride A suspension of thiourea (38 g, 50.0 mmole) in dry tetrahydrofuran (40 ml) was cooled to 0° C. under argon and was treated dropwise with 4-methoxybenzyl chloride (8.0 g, 50.0 mmole). After the addition was completed, the cooling bath was removed and the reaction was allowed to stir at room temperature for 2 hours. It was then heated at 60°-65° C. for 4 hours whereupon a colorless voluminous precipitate was formed. The reaction was allowed to cool down to room temperature and was diluted with anhydrous ether. The solid was filtered off and washed with anhydrous ether to give 10.92 g of 2-(4-methoxybenzyl)-2-thiopseudourea, hydrochloride, melting point 161°-163.5° C.

Analysis Calc'd. for $C_9H_{12}N_2OS \cdot HCl$: C, 46.45; H, 5.63; N, 12.04; S, 13.78; Cl, 15.23. Found: C, 46.48; H, 5.64; N, 12.25; S, 13.74; Cl, 15.31

(B)

1,4-Dihydro-2-[[(4-methoxyphenyl)methyl]thio]-6-methyl-4-(3-nitrophenyl)-5-pyrimidinecarboxylic acid, methyl ester A solution of 2-[(3-nitrophenyl)methylene]-3-oxobutanoic acid, methyl ester (5.0 g, 0.02 mole) in 20 ml of dimethylformamide under argon at room temperature was treated with S-(4-methoxybenzyl)thiopseudourea, hydrochloride (4.65 g, 0.02 mole) and sodium acetate (1.64 g, 0.02 mole). The mixture was then heated at 65±5° C. for 3 hours. Upon cooling, ethyl acetate was added and a small amount of solids were filtered. The filtrate was washed with water (twice), aqueous sodium bicarbonate and saturated brine. The aqueous washes were extracted with fresh ethyl acetate. The combined filtrate and washings were dried (magnesium sulfate) and concentrated in vacuo to give about 9 g of crude product. Crystallization from acetone-isopropyl ether gave 6.8 g of product, melting point 125°-127.5° C., tlc, silica gel, ethyl acetate/hexane (1:1), $R_f$=0.48.

Analysis Calc'd. for $C_{21}H_{21}N_3O_5S$: C, 59.00; H, 4.95; N, 9.83; S, 7.50. Found: C, 58.86; H, 4.82; N, 9.51; S, 7.25

(C)

1-[(Ethylamino)carbonyl]-1,6-dihydro-2-[[(4-methoxyphenyl)methyl]thio]-4-methyl-6-(3-nitrophenyl)-5-pyrimidinecarboxylic acid, methyl ester A solution of 1,4-dihydro-2-[[(4-methoxyphenyl)methyl]thio]-6-methyl-4-(3-nitrophenyl)-5-pyrimidinecarboxylic acid, methyl ester (1.5 g, 3.5 mmole) in acetone under argon at room temperature was treated with ethyl isocyanate (0.5 ml, 0.45 g, 6.3 mmole) and powdered potassium carbonate (50 mg, 0.36 mmole). Examination of the reaction mixture using thin layer chromatography (tlc) (dichloromethane/methanol, 95:5) showed a new spot at higher $R_f$ which did not increase after 1 to 2 hours. Volatiles were evaporated in vacuo and the residue was partitioned between ethyl acetate and water. The organic fraction was washed with water, 1N hydrochloric acid, water and saturated brine. The aqueous fractions were back-extracted with fresh ethyl acetate. The combined organic fractions were dried (magnesium sulfate) and concentrated in vacuo to give 1.6 g of crude product.

Flash chromatography on 250 ml of silica gel and elution with dichloromethane/hexanes (2:1 to 3:1) followed by dichloromethane/methanol (99.5:0.5) gave 0.94 g of the title compound.

(D)
3-[(Ethylamino)carbonyl]-1,2,3,4-tetrahydro-6-methyl-4-(3-nitrophenyl)-2-thioxo-5-pyrimidinecarboxylic acid, methyl ester 1-[(Ethylamino)carbonyl]-1,6-dihydro-2-[[(4-methoxyphenyl)methyl]thio]-4-methyl-6-(3-nitrophenyl)-5-pyrimidinecarboxylic acid, methyl ester (0.94 g, 1.89 mmole) in 10 ml of dry dichloromethane under argon at room temperature was treated with trifluoroacetic acid (0.5 ml, 0.74 g, 6.5 mmole) and ethanethiol (0.35 ml, 0.29 g, 4.67 mmole) and the mixture was allowed to stir overnight. Volatiles were removed in vacuo and the residue upon trituration with isopropyl ether, gave 0.59 g of the title compound, melting point 244°–246° C.

Analysis Calc'd. for $C_{16}H_{18}N_4O_5S$: C, 50.79; H, 4.79; N, 14.81; S, 8.47. Found: C, 50.82; H, 4.86; N, 14.54; S, 8.54

EXAMPLE 2

3-[(Dimethylamino)carbonyl]-1,2,3,4-tetrahydro-6-methyl-4-(3-nitrophenyl)-2-oxo-5-pyrimidinecarboxylic acid, 1-methylethyl ester (A)
1,4-Dihydro-2-methoxy-6-methyl-4-(3-nitrophenyl)-5-pyrimidinecarboxylic acid, 1-methylethyl ester A reaction mixture containing 2-[(3-nitrophenyl)methylene]-3-oxobutanoic acid, 1-methylethyl ester (10.0 g, 36.0 mmol), sodium bicarbonate (8.40 g, 108 mmol), and O-methylpseudourea hydrogen sulfate (8.06 g, 46.8 mmol) in dimethylformamide (54 ml) was heated at 60° C. under argon for about 2½ days. The reaction mixture was diluted with water and extracted with ethyl acetate. The organic phase was washed with water (six times) and saturated sodium chloride, dried (potassium carbonate) and evaporated. The residue was passed through a short pad of silica gel and crystallized from isopropyl ether/hexanes to give the title compound as yellow crystals (8.04 g).

(B)
1-[(Dimethylamino)carbonyl]-1,6-dihydro-2-methoxy-4-methyl-6-(3-nitrophenyl)-5-pyrimidinecarboxylic acid, 1-methylethyl ester A solution of 1,4-dihydro-2-methoxy-6-methyl-4-(3-nitrophenyl)-5-pyrimidinecarboxylic acid, 1-methylethyl ester (3.34 g, 10.0 mmol) and distilled triethylamine (6.3 ml, 45 mmol) in dichloromethane (10 ml) in an ice bath under argon was treated dropwise via syringe with 1.3M phosgene in benzene solution (9.2 ml, 12 mmol) over 3 to 5 minutes. After stirring at 0° C. for 1.5 hours, the reaction mixture was treated with 40% aqueous dimethylamine (3.3 ml, 15 mmol), capped with a septum, and stirred at room temperature for about 2½ days. The reaction was then evaporated and partitioned between ethyl acetate and water. The organic phase was washed with saturated sodium chloride, dried (potassium carbonate), and evaporated to give the title compound (crude) as a brown oil (4.75 g).

(C)
3-[(Dimethylamino)carbonyl]-1,2,3,4-tetrahydro-6-methyl-4-(3-nitrophenyl)-2-oxo-5-pyrimidinecarboxylic acid, 1-methylethyl ester A solution of crude 1-[(dimethylamino)carbonyl]-1,6-dihydro-2-methoxy-4-methyl-6-(3-nitrophenyl)-5-pyrimidinecarboxylic acid, 1-methylethyl ester (2.27 g), in tetrahydrofuran/methanol (20 ml each) was treated with 5N hydrochloric acid (3.0 ml, pH1) and stirred at room temperature for 1.0 hour. The reaction was then evaporated and partitioned between ethyl acetate and water. The organic phase was washed with saturated sodium chloride, dried (magnesium sulfate), and evaporated. The residue was crystallized from dichloromethane/isopropyl ether to give the title compound as colorless crystals (1.55 g), melting point 165°–166° C.

Analysis Calc'd. for $C_{18}H_{22}N_4O_6$: C, 55.38; H, 5.68; N, 14.35. Found: C, 55.44; H, 5.70; N, 14.27

EXAMPLE 3

3-[(Dimethylamino)carbonyl]-1,2,3,4-tetrahydro-6-methyl-4-(3-nitrophenyl)-2-thioxo-5-pyrimidinecarboxylic acid, ethyl ester (A)
1,4-Dihydro-2-[[(4-methoxyphenyl)methyl]thio]-6-methyl-4-(3-nitrophenyl)-5-pyrimidinecarboxylic acid, ethyl ester A mixture of 13.58 g of 2-(3-nitrophenyl)methylene]-3-oxobutanoic acid, ethyl ester, 12.0 g of S-[(4-methoxyphenyl)methyl]thiopseudourea, hydrochloride and 4.18 g (0.051 mole) of sodium acetate in 90 ml of dimethylformamide was stirred and heated at 70° C. for 4 hours. After cooling, ether was added followed by washing with water, sodium bicarbonate and brine. The dried solution was evaporated to give an oil which was treated with isopropyl ether to form 18.8 g of a cream colored solid, melting point 95°–97° C.

(B)
1,6-Dihydro-2-[[(4-methoxyphenyl)methyl]thio]-4-methyl-1-[(dimethylamino)carbonyl]-6-(3-nitrophenyl)-5-pyrimidinecarboxylic acid, ethyl ester A solution of 1,4-dihydro-2-[[(4-methoxyphenyl)methyl]thio]-6-methyl-4-(3-nitrophenyl)-5-pyrimidinecarboxylic acid, ethyl ester (0.5 g, 1.1 mmole) in 10 ml of dry tetrahydrofuran under argon at 0°–5° C. was treated with pyridine (1.0 ml, 12.6 mmole), then with phosgene (1.16 ml of 12.5% in benzene, 1.47 mmol). After 0.5 hours at 0°–5° C., dimethylamine (1 ml of 40% aqueous, excess) was added. Reaction was complete within 0.5 hours. The mixture was diluted with ethyl acetate and washed with 1N hydrochloric acid, water and saturated brine. The aqueous washes were back extracted with fresh ethyl acetate. The combined organic extracts were dried (magnesium sulfate) and concentrated in vacuo to give 0.6 g of essentially homogeneous product.

(C)
3-[(Dimethylamino)carbonyl]-1,2,3,4-tetrahydro-6-methyl-4-(3-nitrophenyl)-2-thioxo-5-pyrimidinecarboxylic acid, ethyl ester A solution of 1,6-dihydro-2-[[(4-methoxyphenyl)methyl]thio]-4-methyl-1-[(dimethylamino)carbonyl]-6-(3-nitrophenyl)-5-pyrimidinecarboxylic acid, ethyl ester (1.26 g, 2.46 mmole) in dry dichloromethane under argon at room temperature was treated with trifluoroacetic acid (0.55 ml, 0.82 g, 7.18 mmole) and ethanethiol (0.36 ml, 0.30 g, 4.78 mmole). The reaction was complete in 2 hours. Volatiles were evaporated in vacuo and the residue, upon trituration with hot isopropyl ether, gave 0.82 g of material. Dissolution of this material in chloroform and filtration to remove some dark insolubles gave, upon final isopropyl ether trituration, 0.80 g of homogeneous product.

Analysis Calc'd. for $C_{17}H_{20}N_4O_5S$: C, 52.03; H, 5.14; N, 14.28; S, 8.17. Found: C, 52.01; H, 5.19; N, 14.23; S, 7.93

EXAMPLE 4

1,2,3,4-Tetrahydro-6-methyl-3-[[methyl(phenylmethyl-)amino]carbonyl]-4-(3-nitrophenyl)-2-oxo-5-pyrimidinecarboxylic acid, 1-methylethyl ester (A)

1,6-Dihydro-1-[[methyl(phenylmethyl)amino]carbonyl]-2-methoxy-4-methyl-6-(3-nitrophenyl)-5-pyrimidinecarboxylic acid, 1-methylethyl ester A solution of 1,4-dihydro-2-methoxy-6-methyl-4-(3-nitrophenyl)-5-pyrimidinecarboxylic acid, 1-methylethyl ester (3.34 g, 10 mmol; see Example 2A) and dry triethylamine (6.3 ml, 45 mmol) in dichloromethane (10 ml) in an ice bath under argon was treated dropwise via syringe with 1.3M phosgene in benzene solution (9.2 ml, 12 mmol). The resulting mixture was stirred in the bath for 20 hours. After cooling to 0° C. with a fresh ice bath, the mixture was treated with benzylmethylamine (1.95 ml, 15 mmol) and stirred at room temperature overnight. The reaction was then diluted with dichloromethane and washed with water, saturated sodium chloride, dried (potassium carbonate) and evaporated. The residue was passed through a short pad of silica, eluting with 20% acetone/hexanes. The fractions were combined evaporated and triturated with isopropyl ether to give white crystals (4.11 g), melting point 145°–146° C. (softens 140° C.).

(B)

1,2,3,4-Tetrahydro-6-methyl-3-[[methyl(phenylmethyl)amino]carbonyl]-4-(3-nitrophenyl)-2-oxo-5-pyrimidinecarboxylic acid, 1-methylethyl ester A suspension of 1,6-dihydro-1-[[methyl(phenylmethyl)amino]carbonyl]-2-methoxy-4-methyl-6-(3-nitrophenyl)-5-pyrimidinecarboxylic acid, 1-methylethyl ester (1.81 g, 3.92 mmol) in tetrahydrofuran/methanol (40 ml each) was treated with 5N hydrochloric acid (4.0 ml). The resulting solution was stirred at room temperature for 1.5 hours, partially evaporated and partitioned between saturated sodium bicarbonate and chloroform. The organic phase was washed with saturated sodium chloride, dried (magnesium sulfate) and evaporated. The residue was crystallized from dichloromethane/isopropyl ether to give white crystals (1.684 g), melting point 159°–161° C. TLC (7% methanol/dichloromethane) single elongated spot, $R_f=0.54$.

Analysis Calc'd. for $C_{24}H_{26}N_4O_6$: C, 61.79; H, 5.62; N, 12.01. Found: C, 61.95; H, 5.64; N, 11.91

EXAMPLE 5

1,2,3,4-Tetrahydro-6-methyl-3-[(methylamino)carbonyl]-4-(3-nitrophenyl)-2-oxo-5-pyrimidinecarboxylic acid, 1-methylethyl ester A solution of 1,4-dihydro-2-methoxy-6-methyl-4-(3-nitrophenyl)-5-pyrimidinecarboxylic acid, 1-methylethyl ester (5.00 g, 15.0 mmol; see Example 2A) and dry triethylamine (5.9 ml, 45 mmol) in distilled dichloromethane (45 ml) at 0° C. under argon was treated dropwise via syringe with 1.2M phosgene in benzene (15.0 ml, 18.0 mmol). After stirring at 0° C. for 3.5 hours, the reaction mixture was treated with 40% aqueous methylamine (1.94 ml, 22.5 mmol). After 0.75 hour, the reaction was quenched with 1N hydrochloric acid (15 ml, pH 1) and partially evaporated. The remaining mixture was diluted with tetrahydrofuran (50 ml) and methanol (25 ml), and treated with more 1N hydrochloric acid (15 ml). After two hours stirring at room temperature, the reaction mixture was partially evaporated. It was then extracted with ethyl acetate. The combined organic phases were washed with saturated sodium bicarbonate, saturated sodium chloride, and evaporated. The organic residue was crystallized from warm ethyl acetate/hexanes to give white crystals (3.47 g). This material was crystallized from dichloromethane/isopropyl ether to give colorless crystals (3.29 g), melting point 204°–205° C. Recrystallization from ethyl acetate/hexnaes gave colorless crystals (2.588 g), melting point 205°–206° C. TLC (5% methanol/dichloromethane) single spot, $R_f=0.45$; visualized with vanillin and heat.

Analysis Calc'd. for $C_{17}H_{20}N_4O_6$: C, 54.25; H, 5.36; N, 14.89. Found: C, 54.40; H, 5.23; N, 14.72

EXAMPLE 6

3-(Aminocarbonyl)-1,2,3,4-tetrahydro-6-methyl-4-(3-nitrophenyl)-2-oxo-5-pyrimidinecarboxylic acid, 1-methylethyl ester (A)

1-Carbamoyl-1,6-dihydro-2-methoxy-4-methyl-6-(3-nitrophenyl)-5-pyrimidinecarboxylic acid, 1-methylethyl ester A solution of 1,4-dihydro-2-methoxy-6-methyl-4-(3-nitrophenyl)-5-pyrimidinecarboxylic acid, 1-methylethyl ester (5.00 g, 15.0 mmol; see Example 2A) and triethylamine (5.88 g; 45.0 mmol) in dichloromethane (45 ml) at 0° C. under argon was treated via syringe with a 1.2M solution of phosgene in benzene (15.0 ml, 18.0 mmol). After stirring at 0° C. for 3.5 hours, the reaction was treated with concentrated ammonium hydroxide (1.52 ml, 22.5 mmol). After two hours at room temperature, the reaction was treated with more concentrated ammonium hydroxide (0.5 ml, 7.5 mmol) and stirred at room temperature overnight. The reaction was then diluted with dichloromethane and washed with water and saturated sodium chloride. The organic phase was concentrated and flash chromatographed to give the title compound as a brittle yellow foam (2.83 g).

(B)

3-(Aminocarbonyl)-1,2,3,4-tetrahydro-6-methyl-4-(3-nitrophenyl)-2-oxo-5-pyrimidinecarboxylic acid, 1-methylethyl ester A solution of 1-carbamoyl-1,6-dihydro-2-methoxy-4-methyl-6-(3-nitrophenyl)-5-pyrimidinecarboxylic acid, 1-methylethyl ester (2.82 g, 7.49 mmol) in tetrahydrofuran (30 ml) and methanol (15 ml) was treated with 1N hydrochloric acid (10 ml, pH 1) and stirred at room temperature for 2.0 hours. The reaction was quenched with saturated sodium bicarbonate and partially evaporated. The mixture was diluted with ethyl acetate, washed with water and saturated sodium chloride, dried (potassium carbonate), and evaporated. The residue was crystallized from ethyl acetate to give colorless crystals (1.44 g). Recrystallization from ethyl acetate failed to remove the impurity. Recrystallization from acetonitrile removed the impurity but recovery was poor (0.58 g). The compound was then recombined and flash chromatographed using 15% acetone and dichloromethane. Trituration with ether gave the title compound as colorless crystals (1.242 g), melting point 206°–207° C. TLC (15% acetone/dichlormethane) single spot, $R_f=0.50$. TLC (methanol/dichloromethane) single spot $R_f=0.38$.

Analysis Calc'd. for $C_{16}H_{18}N_4O_6$: C, 53.04; H, 5.01; N, 15.46. Found: C, 52.78; H, 4.90; N, 15.24

EXAMPLE 7

1,2,3,4-Tetrahydro-6-methyl-4-(3-nitrophenyl)-2-oxo-3-(1-piperidinylcarbonyl)-5-pyrimidinecarboxylic acid, 1-methylethyl ester A solution of 1,4-dihydro-2-methoxy-6-methyl-4-(3-nitrophenyl)-5-pyrimidinecarboxylic acid, 1-methylethyl ester (3.50 g, 10.5 mmol; see Example 2A) and triethylamine (4.39 ml, 31.5 mmol) in dichloromethane (33 ml) at 0° C. under argon was treated via syringe with a 1.2M solution of phosgene in benzene (10.5 ml, 12.6 mmol). After stirring at 0° C. for 3.5 hours, the reaction was treated with piperidine (1.56 ml, 15.7 mmol) and stirred at room temperature overnight under argon. The reaction was then diluted with dichloromethane, washed with water, and evaporated. The residue was flash chromatographed to give the desired intermediate as a yellow foam (4.94 g). This foam was taken up in tetrahydrofuran (50 ml) and methanol (30 ml) and treated with 1N hydrochloric acid (15 ml, pH 1). After stirring at room temperature for 2.5 hours, the reaction was partially evaporated. The residue was diluted with ethyl acetate and washed with saturated sodium bicarbonate, saturated sodium chloride, dried (magnesium sulfate) and evaporated. The residue was crystallized from dichloromethane/isopropyl ether to give a light yellow solid (4.12 g). This material was recrystallized to give the title compound as colorless crystals (2.75 g), melting point 164°–165° C. TLC (15% acetone/dichloromethane) single spot, $R_f=0.45$.

Analysis Calc'd. for $C_{21}H_{26}N_4O_6$: C, 58.60; H, 6.09; N, 13.02. Found: C, 58.61; H, 6.00; N, 12.91

EXAMPLE 8

1,2,3,4-Tetrahydro-6-methyl-3-[[(1-methylethyl)amino]carbonyl]-4-(3-nitrophenyl)-2-oxo-5-pyrimidinecarboxylic acid, 1-methylethyl ester A solution of 1,4-dihydro-2-methoxy-6-methyl-4-(3-nitrophenyl)-5-pyrimidinecarboxylic acid, 1-methylethyl ester (2.10 g, 6.3 mmol; see Example 2A) and triethylamine (2.64 ml, 19 mmol) in dichloromethane (19 ml) at 0° C. under argon was treated via syringe with a 1.2M solution of phosgene in benzene (6.3 ml, 7.6 mol). After stirring at 0° C. for 3.5 hours, the reaction was treated with isopropylamine (0.81 ml, 9.5 mmol) and stirred at room temperature under argon overnight. The reaction was then diluted with dichloromethane, washed with water and saturated sodium chloride and evaporated. The residue was taken up in tetrahydrofuran/methanol (18 ml each), treated with 1N hydrochloric acid (10 ml, pH 1) and stirred at room temperature for 2 hours. The reaction was then partially evaporated, and partitioned between ethyl acetate and water. The organic phase was washed with saturated sodium bicarbonate, saturated sodium chloride, dried (magnesium sulfate) and evaporated. The residue was crystallized from isopropyl ether/hexanes to give yellow crystals (2.16 g, 85%). This material was recrystallized from dichloromethane/isopropyl ether to give colorless crystals (1.759 g) melting point 145°–146° C. TLC (5% ethyl acetate/dichloromethane) single spot, $R_f=0.49$.

Analysis Calc'd. for $C_{19}H_{24}N_4O_6$: C, 56.43; H, 5.98; N, 13.85. Found: C, 56.18; H, 5.89; N, 13.45

EXAMPLE 9

1,2,3,4-Tetrahydro-6-methyl-4-(3-nitrophenyl)-2-oxo-3-[[(phenylmethyl)amino]carbonyl]-5-pyrimidinecarboxylic acid, 1-methylethyl ester (A)

1,6-Dihydro-2-methoxy-4-methyl-6-(3-nitrophenyl)-1-[[(phenylmethyl)amino]carbonyl]-5-pyrimidinecarboxylic acid, 1-methylethyl ester A solution of 1,4-dihydro-2-methoxy-6-methyl-4-(3-nitrophenyl)-5-pyrimidinecarboxylic acid, 1-methylethyl ester (5.00 g, 15.0 mmol; see Example 2A) and dry triethylamine (6.27 ml, 45 mmol) in dichloromethane (45 ml) in an ice bath under argon was treated with a 1.2M solution of phosgene in benzene (15.0 ml, 18.0 mmol) via syringe. After stirring 4.0 hours at 0° C., the reaction was treated with benzyl amine (2.46 ml, 22.5 mmol) and stirred at ambient temperature overnight. The reaction was treated with water and saturated sodium chloride. The organic phase was evaporated and flash chromatographed (3% ethyl acetate in dichloromethane) to give the title compound as a yellow foam (6.20 g) TLC (5% ethyl acetate/dichlorolmethane) major spot, $R_f=0.70$.

(B)

1,2,3,4-Tetrahydro-6-methyl-4-(3-nitrophenyl)-2-oxo-3-[[(phenylmethyl)amino]carbonyl]-5-pyrimidinecarboxylic acid, 1-methylethyl ester A solution of 1,6-dihydro-2-methoxy-4-methyl-6-(3-nitrophenyl)-1-[[(phenylmethyl)amino]carbonyl]-5-pyrimidinecarboxylic acid, 1-methylethyl ester (3.00 g, 6.45 mmol) in tetrahydrofuran (50 ml)/methanol (25 ml) was treated with 1 N hydrochloric acid (6.0 ml, pH 1) and stirred at room temperature for 1 hour. The reaction was quenched with saturated sodium bicarbonate and partially evaporated. The residue was partitioned between chloroform and water. The organic phase was washed with saturated sodium chloride, dried (magnesium sulfate) and evaporated. The residue was crystallized from dichloromethane/isopropyl ether. The solids which precipitated were recrystallized to give the title compound as a colorless electrostatic solid (1.84 g), melting point 184°–185° C. TLC (5% ethyl acetate/dichloromethane) single spot, $R_f=0.39$.

Analysis Calc'd. for $C_{23}H_{24}N_4O_6$: C, 61.05; H, 5.35; N, 12.38. Found: C, 60.97; H, 5.36; N, 12.33

EXAMPLE 10

3-[(Ethylamino)carbonyl]-1,2,3,4-tetrahydro-6-methyl-4-(3-nitrophenyl)-2-oxo-5-pyrimidinecarboxylic acid, 1-methylethyl ester A solution of 1,4-dihydro-2-methoxy-6-methyl-4-(3-nitrophenyl)-5-pyrimidinecarboxylic acid, 1-methylethyl ester (2.00 g, 6.00 mmole; see Example 2A) and triethylamine (2.5 ml, 18.0 mmole) in acetonitrile (18 ml) in an ice bath under argon was treated via syringe with a 1.3M solution of phosgene in toluene. The reaction was stirred at 0° C. for 3.0 hours and then treated with a 70% solution of aqueous ethylamine (0.36 ml, 9.0 mmole). After stirring in the ice bath for 3.0 hours, the reaction was evaporated. The residue was taken up in tetrahydrofuran/methanol (24 ml each) and treated with 5N hydrochloric acid (4.0 ml). After stirring at ambient temperature for 1.0 hour, the reaction was partially evaporated and then quenched with saturated sodium bicarbonate. The aqueous phase was extracted with ethyl acetate and washed with saturated sodium chloride. Flash chromatography (5% ethyl acetate in dichloromethane) and crystallization from dichloromethane/isopropyl ether gave colorless crystals (1.22 g), melting point 153°–155° C. TLC (5% ethyl acetate/dichloromethane) single spot, $R_f$=0.26.

Analysis Calc'd. for $C_{18}H_{22}N_4O_6$: C, 55.37; H, 5.68; N, 14.35. Found: C, 55.33; H, 5.66; N, 14.31

EXAMPLE 11

3-[(Dimethylamino)carbonyl]-1,2,3,4-tetrahydro-6-methyl-4-(3-nitrophenyl)-2-oxo-5-pyrimidinecarboxylic acid (A)

1,4-Dihydro-2-methoxy-6-methyl-4-(3-nitrophenyl)-5-pyrimidinecarboxylic acid, t-butyl ester A mixture of 2-[(3-nitrophenyl)methylene]-3-oxobutanoic acid, t-butyl ester (6.80 g, 23.3 mmol), o-methylisourea hydrogen sulfate (5.22 g, 30.3 mmol), and sodium bicarbonate (5.87 g, 69.9 mmol) in dimethylformamide (35 ml) was stirred at room temperature overnight under argon. After 23 hours at room temperature, the reaction was heated at 60° C. (oil bath) for 5.5 hours. It was then partitioned between ethyl acetate and 5% sodium bicarbonate. The organic phase was washed several times with water, washed with saturated sodium chloride, and dried over potassium carbonate. Evaporation gave crude title compound as a light brown oil (9.93 g).

(B)

3-[(Dimethylamino)carbonyl]-1,2,3,4-tetrahydro-6-methyl-4-(3-nitrophenyl)-2-oxo-5-pyrimidinecarboxylic acid, t-butyl ester A solution of 1,4-dihydro-2-methoxy-6-methyl-4-(3-nitrophenyl)-5-pyrimidinecarboxylic acid, t-butyl ester (1.30 g, 3.05 mmol) and dry triethylamine (1.27 ml, 9.15 mmol) in dichloromethane (10 ml) in an ice bath under argon was treated via syringe with a 1.2M solution of phosgene in benzene (3.05 ml, 3.66 mmol). After stirring overnight, the reaction was cooled to 0° C. and treated with 40% aqueous dimethylamine (0.40 ml, 4.57 mmol). The bath was then removed, and the reaction was stirred at room temperature for 3.0 hours. The reaction was diluted with dichloromethane, washed with water, saturated sodium chloride, and evaporated. Flash chromatography (3% ethyl acetate/dichloromethane) gave the desired intermediate as a yellow foam (0.50 g). This compound was taken up in tetrahydrofuran/methanol (6.0 ml each) and treated with 1N hydrochloric acid (2.0 ml, pH 1). The reaction was stirred at ambient temperature for 2.0 hours and evaporated. The residue was taken up in ethyl acetate and washed with saturated sodium bicarbonate, saturated sodium chloride, dried (magnesium sulfate) and evaporated. The residue was crystallized from isopropyl ether/dichloromethane to give the title compound as colorless crystals (265 mg), melting point 187°–188° C.

(C)

3-[(Dimethylamino)carbonyl]-1,2,3,4-tetrahydro-6-methyl-4-(3-nitrophenyl)-2-oxo-5-pyrimidinecarboxylic acid A solution of 3-[(dimethylamino)carbonyl]-1,2,3,4-tetrahydro-6-methyl-4-(3-nitrophenyl)-2-oxo-5-pyrimidinecarboxylic acid, t-butyl ester (230 mg, 0.59 mmol) in chloroform (4.0 ml) was treated with trifluoroacetic acid (1.2 ml) at ambient temperature under argon. After stirring for 2.5 hours, the reaction was evaporated, coevaporated with toluene and crystallized from ethanol/ether to give the title compound as colorless crystals (134 mg), melting point 193°–195° C. TLC (5% methanol/dichloromethane) single spot, $R_f$=0.21.

Analysis Calc'd. for $C_{15}H_{16}N_4O_6$: C, 51.72; H, 4,63; N, 16.08. Found: C, 51.41; H, 4.57; N, 15.73

EXAMPLE 12

3-(Aminocarbonyl)-1,2,3,4-tetrahydro-6-methyl-4-(3-nitrophenyl)-2-oxo-5-pyrimidinecarboxylic acid, ethyl ester (A)

1,4-Dihydro-2-methoxy-6-methyl-4-(3-nitrophenyl)-5-pyrimidinecarboxylic acid, ethyl ester A mixture of 2-[(3-nitrophenyl)methylene]-3-oxobutanoic acid, ethyl ester (16.46 g, 62.6 mmol), o-methylisourea hydrogen sulfate (14.00 g, 81.4 mmol), and sodium bicarbonate (15.8 g, 18.8 mmol) in dimethylformamide (9.4 ml) was heated at 70° C. (oil bath) under argon overnight. The cooled reaction was diluted with water and extracted with ethyl acetate. The organic phase was washed several times with water, washed with saturated sodium chloride, dried (potassium carbonate) and evaporated. The residue was passed through a pad of silica gel, crystallized from isopropyl ether/hexanes and then triturated with 60% isopropyl ether hexanes (50 ml) to give 1,4-dihydro-2-methoxy-6-methyl-4-(3-nitrophenyl)-5-pyrimidinecarboxylic acid, ethyl ester as light yellow crystals (12.32 g), melting point 101°–103° C.

(B)

3-(Aminocarbonyl)-1,2,3,4-tetrahydro-6-methyl-4-(3-nitrophenyl)-2-oxo-5-pyrimidinecarboxylic acid, ethyl ester A solution of 1,4-dihydro-2-methoxy-6-methyl-4-(3-nitrophenyl)-5-pyrimidinecarboxylic acid, ethyl ester (est. 19.8 mmol) and dry triethylamine (11.1 ml, 80 mmol) in acetonitrile (40 ml) in an ice bath under argon was treated with a 1.2M solution of phosgene in toluene (20 ml, 24 mmol) via syringe. After stirring at 0° C. for 2.0 hours, the reaction was treated with a 0.7M solution of ammonia in tetrahydrofuran (46 ml, 32 mmol) and stirred at 0° C. for 1.3 hours. Nitrogen was bubbled through the reaction and it was partially evaporated. The residuals were diluted with tetrahydrofuran (100 ml) and methanol (50 ml) and treated with 1N hydrochloric acid (40 ml, pH 1). After 1.0 hour stirring, the reaction was quenched with saturated sodium bicarbonate. The organic extracts were washed with saturated sodium chloride, dried (magnesium sulfate), and evaporated. The residue was crystallized from dichloromethane/isopropyl ether to give yellow crystals (2.7 g). This solid material was thoroughly triturated with acetonitrile to give the title compound as colorless crystals (2.254 g), melting point 213°–215° C. TLC (40% acetone/hexane) single spot, $R_f$=0.42.

Analysis Calc'd. for $C_{15}H_{16}N_4O_6$: C, 51.72; H, 4.63; N, 16.08. Found: C, 51.78; H, 4.67; N, 15.95

EXAMPLE 13

3-(Aminocarbonyl)-1,2,3,4-tetrahydro-6-methyl-2-oxo-4-[2-(trifluoromethyl)phenyl]-5-pyrimdinecarboxylic acid, ethyl ester (A)

1,4-Dihydro-2-methoxy-6-methyl-4-[(2-trifluoromethyl)phenyl]-5-pyrimidinecarboxylic acid, ethyl ester A solution of 2-[[2-(trifluoromethyl)phenyl]methylene]-3-oxobutanoic acid, ethyl ester (2.86 g; 10.0 mmoles) in dry dimethylformamide (10 ml) under argon was treated with o-methylisourea hydrogen sulfate (2.10 g; 12.2 mmoles) and sodium acetate (2.0 g; 12.2 mmoles). The resulting suspension was allowed to stir at room temperature overnight and then heated at 55° C. for 6 hours. The reaction was diluted with ethyl acetate, filtered and the filtrate was washed with water, sodium bicarbonate and brine. After drying over anhydrous magnesium sulfate, the solvent was evaporated to give a yellow foam. It was purified by flash chromatography (5% ethyl acetate in methylene chloride) to provide the title compound (2.17 g) as a colorless thick oil which solidified on standing. This product was used for the next reaction without further purification.

(B)

3-(Aminocarbonyl)-1,2,3,4-tetrahydro-6-methyl-2-oxo-4-[2-(trifluoromethyl)phenyl]-5-pyrimidinecarboxylic acid, ethyl ester A solution of 1,4-dihydro-2-methoxy-6-methyl-4-[(2-trifluoromethyl)phenyl]-5-pyrimidinecarboxylic acid, ethyl ester (2.85 g, 8.63 mmol) and dry triethylamine (4.81 ml, 34.5 mmol) in acetonitrile (20 ml) at 0° C. under argon was treated with a 1.2M solution of phosgene in toluene (8.6 ml, 10.3 mmol) via syringe. After stirring at 0° C. for 2.0 hours, the reaction was treated with a 0.7M solution of ammonia in tetrahydrofuran (19.7 ml, 13.8 mmol) and stirred at 0° C. for 1.5 hours. Nitrogen was bubbled through the reaction and it was partially evaporated. The residuals were diluted with tetrahydrofuran (40 ml) and methanol (20 ml) and treated with 1N hydrochloric acid (20 ml, pH 1). After 1.5 hour stirring, the reaction was quenched with saturated sodium bicarbonate and partially evaporated. The aqueous phase was extracted with ethyl acetate. The combined organic layers were washed with saturated sodium chloride and evaporated. The crude product was flash chromatographed (5–15% acetone/dichloromethane) and triturated with ether (twice) to give the title compound as colorless crystals (790 mg). Crystals shrank over 105°–115° C. range, then slowly melted 155°–160° C. TLC (3% acetone/ether) single spot, $R_f$=0.61.

Analysis Calc'd. for $C_{16}H_{16}F_3N_3O_4$: C, 51.75; H, 4.34; N, 11.32; F, 15.35. Found: C, 52.05; H, 4.50; N, 10.99; F, 15.64

EXAMPLE 14

[3(S)]-1,2,3,4-Tetrahydro-6-methyl-4-(3-nitrophenyl)-2-oxo-3-[[(1-phenylethyl)amino]carbonyl]-5-pyrimidinecarboxylic acid, 1-methylethyl ester, isomers A and B A solution of 1,4-dihydro-2-methoxy-6-methyl-4-(3-nitrophenyl)-5-pyrimidinecarboxylic acid, 1-methylethyl ester (2.0 g, 6.0 mmoles; see Example 2A) in dichloromethane (10 ml) and triethylamine (4.2 ml) was allowed to cool to 0° C. under argon and was treated dropwise with phosgene solution in toluene (6 ml of 1.3M solution). A colorless thick precipitate was formed. The reaction was allowed to stir at 0° C. for 30 minutes and then treated dropwise with (S)-(−)-α-methylbenzylamine (800 mg, 6.6 mmoles). The ice bath was removed and the reaction was allowed to stir at room temperature for 3 hours. The solvent was evaporated and the residue was dissolved in methanol-tetrahydrofuran (10 ml of 1:1 mixture). The resulting solution was treated with 2N hydrochloric acid (2 ml) and allowed to stir at room temperature for 1 hour. The solvent was removed and the residue was extracted with dichloromethane. The combined extracts were washed with water, sodium bicarbonate and brine. After drying over anhydrous magnesium sulfate, the solvent was evaporated and the residue was passed through a short column of silica gel (ethyl acetate/dichloromethane: 5/95). The product was crystallized from dichloromethane-isopropyl ether to provide colorless solid (isomer B: 619 mg). Recrystallization from the same solvent system provided the analytically pure isomer B, melting point 197.5°–198.5° C., $[\alpha]_D = +139°$ (1% chloroform). The mother liquor from the first crystallization was evaporated and the residue was crystallized again from dichloromethaneisopropyl ether to give a mixture of isomers A and B (301 mg). The resulting mother liquor was concentrated and crystallized from ether-hexanes to yield pure isomer A (501 mg), melting point 94°–97° C., $[\alpha]_D = -232°$ (1%, chloroform).

Analysis Calc'd. for $C_{24}H_{26}N_4O_6$: C, 61.79; H, 5.62; N, 12.01. Found (Isomer A): C, 61.94; H, 5.54; N, 11.97. Found (Isomer B): C, 61.90; H, 5.57; N, 11.99

EXAMPLE 15

[3(R)]-1,2,3,4-Tetrahydro-6-methyl-4-(3-nitrophenyl)-2-oxo-3-[[(1-phenylethyl)amino]carbonyl]-5-pyrimidinecarboxylic acid, 1-methylethyl ester, isomers A and B A solution of 1,4-dihydro-2-methoxy-6-methyl-4-(3-nitrophenyl)-5-pyrimidinecarboxylic acid, 1-methylethyl ester (2.0 g, 6.0 mmoles; see Example 2A) in dichloromethane (10 ml) and triethylamine (4.2 ml) was allowed to cool down to 0° C. under argon and was treated dropwise with phosgene solution in toluene (6 ml of 1.3M solution). A colorless thick precipitate was formed. The reaction was allowed to stir at 0° C. for 30 minutes and then treated dropwise with (R)-(+)-α-methylbenzylamine (800 mg, 6.6 mmoles). The ice bath was removed and the reaction was allowed to stir at room temperature for 3 hours. The solvent was evaporated and the residue was dissolved in methanol-tetrahydrofuran (10 ml of 1:1 mixture). The resulting solution was treated with 2N hydrochloric acid (2 ml) and allowed to stir at room temperature for 1 hour. The solvent was removed and the residue was extracted with dichloromethane. The combined extracts were washed with water, sodium bicarbonate and brine. After drying over anhydrous magnesium sulfate, the solvent was evaporated and the residue was passed through a short column of silica gel (ethyl acetate/dichloromethane: 5/95). The product was crystallized from dichloromethane-isopropyl ether to provide colorless solid (isomer B: 530 mg). Recrystallization from the same solvent system provided the analytically pure isomer B (380 mg), melting point 187°–188° C., $[\alpha]_D = -125°$ (1%, chloroform). The mother liquor from the first crystallization was evaporated and the residue was crystallized against from dichloromethane-isopropyl ether to give a mixture of isomers A and B (380 mg). The resulting mother liquid was concentrated and crystallized from isopropyl ether-hexanes to yield isomer A (325 mg), melting point 145°–149° C., $[\alpha]_D = +236°$ (1%, chloroform).

Analysis Calc'd. for $C_{24}H_{26}N_4O_6$: C, 61.79; H, 5.62; N, 12.02. Found (Isomer A): C, 61.84; H, 5.53; N, 12.00. Found (Isomer B): C, 61.90; H, 5.57; N, 11.99

EXAMPLE 16

3-(Aminocarbonyl)-4-(2,1,3-benzoxadiazol-4-yl)-1,2,3,4-tetrahydro-6-methyl-2-oxo-5-pyrimidinecarboxylic acid, 1-methylethyl ester (A)

4-(2,1,3-Benzoxadiazol-4-yl)-1,4-dihydro-2-methoxy-6-methyl-5-pyrimidinecarboxylic acid, 1-methylether ester A mixture of 2-[(2,1,3-benzoxadiazol-4-yl)methylene]-3-oxobutanoic acid, 1-methylethyl ester (2.04 g, 7.43 mmol), sodium bicarbonate (1.87 g, 22.3 mmol) and O-methylisourea hydrogen sulfate (1.66 g, 9.66 mmol) in dimethylformamide (7.5 ml) was heated at 65° C. (oil bath) overnight under argon. The reaction was then diluted with ethyl acetate, washed several times with water, washed with saturated sodium chloride, dried (potassium carbonate), and evaporated. The residue was flash chromatographed over Merck silica gel (400 ml) eluting with 10% ethyl acetate/dichloromethane to give 4-(2,1,3-benzoxadiazol-4-yl)-1,4-dihydro-2-methoxy-6-methyl-5-pyrimidinecarboxylic acid, 1-methylethyl ester as a dark solid (0.60 g, 25%). TLC (10% ethyl acetate/dichloromethane) single spot, $R_f = 0.17$.

(B)

4-(2,1,3-Benzoxadiazol-4-yl)-1,2,3,4-tetrahydro-6-methyl-3,5-pyrimidinedicarboxylic acid, 5-(1-methylethyl), 3-(4-nitrophenyl)ester A solution of 4-(2,1,3-benzoxadizol-4-yl)-1,4-dihydro-2-methoxy-6-methyl-5-pyrimidinecarboxylic acid, 1-methylethyl ester (0.60 g, 1.82 mmol) and pyridine (0.88 ml, 10.9 mmol) in dichloromethane (10 ml) in an ice bath under argon was treated dropwise, via addition funnel, with a solution of 4-nitrophenylchloroformate (403 mg, 2.00 mmol) in dichloromethane (10 ml). The reaction was then stirred at 0° C. for one hour and evaporated. The residue was then taken up in tetrahydrofuran (20 ml) and methanol (10 ml) and treated with 3N hydrochloric acid (2 ml, pH 1). After stirring at ambient temperature for 45 minutes, the reaction was evaporated to near dryness, cooled in an ice bath, and quenched with saturated sodium bicarbonate. This mixture was extracted with ethyl acetate. The organic phase was washed with saturated sodium chloride, dried (potassium carbonate) and evaporated to give 4-(2,1,3-benzoxadiazol-4-yl)-1,2,3,4-tetrahydro-6-methyl-3,5-pyrimidinedicarboxylic acid, 5-(1-methylethyl), 3-(4-nitrophenyl)ester as a brown solid (0.63 g, 74%). TLC (40% acetone/hexanes) major spot, $R_f = 0.33$.

(C)

3-(Aminocarbonyl)-4-(2,1,3-benzoxadiazol-4-yl)-1,2,3,4-tetrahydro-6-methyl-2-oxo-5-pyrimidinecarboxylic acid, 1-methylethyl ester A solution of 4-(2,1,3-benzoxadiazol-4-yl)-1,2,3,4-tetrahydro-6-methyl-2-oxo-3,5-pyrimidinedicarboxylic acid, 5-(1-methylethyl), 3-(4-nitrophenyl)ester (0.63 g, 1.35 mmol) in distilled tetrahydrofuran (14 ml) in an ice bath under argon was treated with a 0.7M solution of ammonia in tetrahydrofuran (2.5 ml, 1.75 mmol) and stirred at 0° C. for one hour. The reaction was then evaporated and flash chromatographed over Merck silica gel (150 ml) eluting with 40% ethyl acetate/hexanes to give a yellow foam (109 mg). Crystallization from isopropyl ether/dichloromethane gave 3-(aminocarbonyl)-4-(2,1,3-benzoxadiazol-4-yl)-1,2,3,4-tetrahydro-6-methyl-2-oxo-5-pyrimidinecarboxylic acid, 1-methylethyl ester as free flowing yellow solid (141 mg, 37%), melting point 207°–208° C. TLC (4% methanol/dichloromethane) single spot, $R_f = 0.27$.

EXAMPLE 17

1,2,3,4-Tetrahydro-6-methyl-3-[[(1-methylethyl)amino]carbonyl]-4-(3-nitrophenyl)-2-oxo-5-pyrimidinecarboxylic acid, (S)-1-methyl-2-[methyl(phenylmethyl)amino]ethyl ester, hydrochloride salt (A)

1,4-Dihydro-2-methoxy-6-methyl-4-(3-nitrophenyl)-5-pyrimidinecarboxylic acid, (S)-1-methyl-2-[methyl(phenylmethyl)amino]ethyl ester A mixture of 2-[3-nitrophenyl)methylene]-3-oxobutanoic acid, (S)-1-methyl-2-[methyl(phenylmethyl)amino]ethyl ester (7.4 g, 18.8 mmol), O-methylisourea hydrogen sulfate (3.88 g, 22.5 mmol), and sodium bicarbonate (7.89 g, 94 mmol) in dimethylformamide (19 ml) under argon was heated at 65° C. (oil bath) overnight. The mixture was then partitioned between ether and water. The organic phase was washed several times with water, and then washed with saturated sodium chloride, dried (potassium carbonate) and evaporated. The thick red residue was flash chromatographed over Merck silica eluting with 5–20% acetone/dichloromethane to give 1,4-dihydro-2-methoxy-6-methyl-4-(3-nitrophenyl)-5-pyrimidinecarboxylic acid, (S)-1-methyl-2-[methyl(phenylmethyl)amino]ethyl ester as a thick, dark oil (3.77 g, 44%). TLC (20% acetone/dichloromethane) two spots, $R_f$ 0.34 and 0.47.

(B)

3,4-Dihydro-6-methyl-4-(3-nitrophenyl)-2-oxo-3,5-pyrimidinedicarboxylic acid, 5[(S)-1-methyl-2-[methyl(phenylmethyl)amino)ethyl], 3-(4-nitrophenyl)ester A solution of 1,4-dihydro-2-methoxy-6-methyl-4-(3-nitrophenyl)-5-pyrimidinecarboxylic acid, (S)-1-methyl-2-[methyl(phenylmethyl)amino]ethyl ester (2.20 g, 4.87 mmol) and pyridine (2.36 ml, 29.2 mmol) in dichloromethane (20 ml) in an ice bath under argon was treated dropwise, via addition funnel, with a solution of 4-nitrophenylchloroformate (1.08 g, 5.36 mmol) in dichloromethane (20 ml). The reaction was then stirred in the ice bath for 15 minutes and evaporated. The residue was coevaporated with toluene to remove pyridine. The residue was then taken up in tetrahydrofuran (50 ml) and methanol (25 ml) and treated with 3N hydrochloric acid (5.0 ml, pH 1). After stirring at ambient temperature for 1.5 hours, the reaction was quenched by pouring into cold (ice bath) saturated sodium bicarbonate. After evaporating to near dryness, the mixture was extracted with ethyl acetate. The combined organic phase was washed with saturated sodium chloride, dried (potassium carbonate), and evaporated to give 3,4-dihydro-6-methyl-4-(3-nitrophenyl)-2-oxo-3,5-pyrimidinedicarboxylic acid, 5[(S)-1-methyl-2-[methyl(-phenylmethyl)methyl)amino)ethyl], 3-(4-nitrophenyl)ester as a brown solid (2.38 g, 83%). TLC (10% acetone/dichloromethane) two major spots, $R_f$=0.25 and 0.39.

(C)
1,2,3,4-Tetrahydro-6-methyl-3-[[(1-methylethyl-)amino]carbonyl]-4-(3-nitrophenyl)-2-oxo-5-pyrimidinecarboxylic acid, (S)-1-methyl-2-[methyl(phenylmethyl)amino]ethyl ester, hydrochloride salt A mixture of 3,4-dihydro-6-methyl-4-(3-nitrophenyl)-2-oxo-3,5-pyrimidinedicarboxylic acid, 5[(S)-1-methyl-2-[methyl(phenylmethyl)amino]ethyl], 3-(4-nitrophenyl)ester (2.38 g, 4.04 mmol) and isopropylamine (0.34 g, 4.04 mmol) in acetonitrile (8 ml) was stirred at ambient temperature overnight under argon. The reaction was diluted with ethyl acetate, washed with saturated sodium bicarbonate (three times) and saturated sodium chloride, dried (potassium carbonate), and evaporated. Flash chromatography over Merck silica gel (300 ml) eluting with 5% acetone/dichloromethane gave a yellow foam (0.84 g). The foam was taken up in ether and treated with ethereal hydrogen chloride solution to give 1,2,3,4-tetrahydro-6-methyl-3-[[(1-methylethyl)amino]carbonyl]-4-(3-nitrophenyl)-2-oxo-5-pyrimidinecarboxylic acid, (S)-1-methyl-2-[methyl(-phenylmethyl)amino]ethyl ester, hydrochloride salt, as electrostatic, yellow crystals (672 mg, 30%), melting point 110°-130° C. (decomposes). TLC (10% acetone/-dichloromethane) two spots, $R_f$=0.38 and 0.46.

EXAMPLE 18

1,2,3,4-Tetrahydro-3-[[[(S)-2-ethoxy-2-oxo-1-(phenylmethyl)ethyl]amino]carbonyl]-6-methyl-4-(3-nitrophenyl)-2-oxo-5-pyrimidinecarboxylic acid, 1-methylethyl ester A mixture of 1,4-dihydro-2-methoxy-6-methyl-4-(3-nitrophenyl)-5-pyrimidinecarboxylic acid, 1-methylethyl ester (4.00 g, 12.0 mmol, see Example 2A) and triethylamine (6.69 ml, 48.0 mmol) in an ice bath under argon in acetonitrile (48 ml) was treated dropwise via GT syringe with a 1.3M solution of phosgene in toluene (12.0 ml, 15.6 mmol). After stirring one hour at 0° C., the reaction was treated with L-phenylalanine ethyl ester hydrochloride (3.31 g, 14.4 mmol) and stirred at ambient temperature for one hour. The mixture was then diluted with tetrahydrofuran/methanol (100 ml each) and treated with 3N hydrochloric acid (15 ml, 45 mmol). After stirring at ambient temperature for one hour, the reaction was cooled in an ice bath and quenched with saturated sodium bicarbonate. The resulting mixture was partially evaporated and extracted with ethyl acetate. The organic phase was washed with saturated sodium chloride, dried (magnesium sulfate), and evaporated.

The residue was flash chromatographed over Merck silica gel (600 ml) eluting with 5% ethyl acetate/dichloromethane. This procedure yielded a mixture of both isomers as well as slow isomer only (2.5 g); each as a yellow foam. The slow isomer (B) portion was crystallized from dichloromethane/isopropyl ether to give lightly tanned white crystals (1.30 g, melting point 132°-133° C.). The mother liquor was combined with the mixture of both isomers and recrystallized from dichloromethane/isopropyl ether to give additional slow isomer (0.60 g) as colorless crystals. The filtrate was partially evaporated to give two crops (2.45 g and 1.39 g) of the fast isomer (A). These two crops were combined and recrystallized to give the fast isomer as light, electrostatic needles (1.34 g, 21%), melting point 122°-124° C. TLC (10% ethyl acetate/dichloromethane) single spot, $R_f$=0.59. $[\alpha]_D$=+165° (1%, chloroform). The corresponding slow isomer (B) portions were combined and recrystallized to give colorless, mildly electrostatic needles (1.57 g, 24%) melting point 134°-135° C. TLC (10% ethyl acetate/dichloromethane) single spot, $R_f$=0.43 $[\alpha]_D$=−155° (1%, chloroform).

Analysis Calc'd. for $C_{27}H_{30}N_4O_8$: C, 60.21; H, 5.61; N, 10.41. Found (fast isomer): C, 60.24; H, 5.66; N, 10.37. (slow isomer): C, 60.17; H, 5.60; N, 10.34

EXAMPLE 19

1,2,3,4-Tetrahydro-6-methyl-3-[[[2-[methyl(phenylmethyl)amino]ethyl]amino]carbonyl]-4-(3-nitrophenyl)-2-oxo-5-pyrimidinecarboxylic acid, 1-methylethyl ester A solution of 1,4-dihydro-2-methoxy-6-methyl-4-(3-nitrophenyl)-5-pyrimidinecarboxylic acid, 1-methylethyl ester (2.00 g, 6.0 mmol; see Example 2A) and triethylamine (1.25 ml, 9.0 mmol) in acetonitrile (18 ml) in an ice bath under argon was treated via GT syringe with a 1.3M solution of phosgene in toluene (6.0 ml, 7.8 mmol). After stirring at 0° C. for 3.0 hours, the reaction was treated with a solution of triethylamine (1.25 ml, 9.0 mmol) and N-benzyl-N-methylaminoethyl amine (1.523 g, 9.0 mmol) in dry tetrahydrofuran (12 ml) under argon via syringe. The reaction was stirred at 0° C. for 1.5 hours, diluted with tetrahydrofuran (24 ml) and methanol (24 ml) and treated with 1N hydrochloric acid (30 ml, pH 1). The reaction was then stirred at room temperature for 2.0 hours and quenched with saturated sodium bicarbonate. The resultant mixture was partially evaporated and extracted with ethyl acetate. The combined organic phases were washed with saturated sodium chloride, dried (magnesium sulfate), and evaporated to give a yellow foam (3.12 g). This material was flash chromatographed (2% methanol/dichloromethane) and crystallized from ether/isopropyl ether to give a colorless solid (1.64 g, 54%), melting point 133°-135° C. TLC (2% methanol/dichloromethane) single spot, $R_f$=0.17.

Analysis Calc'd. for $C_{26}H_{31}N_5O_6$: C, 61.28; H, 6.13; N, 13.74. Found: C, 61.33; H, 6.19; N, 13.49

EXAMPLE 20

(−)-3-[(Dimethylamino)carbonyl]-1,2,3,4-tetrahydro-6-methyl-4-(3-nitrophenyl)-2-oxo-5-pyrimidinecarboxylic acid, 1-methylethyl ester (A)

3,4-Dihydro-2-[[(4-methoxyphenyl)methyl]thio]-6-methyl-4-(3-nitrophenyl)-3,5-pyrimidinedicarboxylic acid, 5-(1-methylethyl)ester, 3-[1-[1,1-dimethylethoxy)carbonyl]-5(S)-(methoxycarbonyl)-3(R)-pyrrolidinyl)ester To a solution of 1,4-dihydro-2-[[(4-methoxyphenyl)methyl]thio]-6-methyl-4-(3-nitrophenyl)-5-pyrimidinecarboxylic acid, 1-methylethyl ester in neat pyridine (44 ml) at room temperature under nitrogen was added phosgene in toluene (1.3M, 1.3 eq., 22 ml).

The reaction mixture was stirred for two hours, and then a solution of 1-[1,1-dimethylethoxy)carbonyl]-4-(trans-hydroxy)-L-proline, methyl ester (8.6 g, 35.2 mmol) in neat pyridine (20 ml) was added dropwise. After stirring for 24 hours at room temperature TLC (1:2:ethyl acetate:hexanes) showed the reaction to be incomplete. Additional 1-[1,1-dimethylethoxy)carbonyl]-4-(trans-hydroxy)-L-proline, methyl ester (5.4 g, 22 mmol) was added as a solution in pyridine (15 ml) and the reaction continued for 24 more hours. The reaction was worked up by diluting with ethyl acetate (100 ml), the organic layer was washed with saturated sodium bicarbonate solution (2×50 ml), sodium dihydrogen phosphate (2×50 ml), and water (2×50 ml), dried over magnesium sulfate, filtered and evaporated in vacuo to afford a foam. Flash chromatography on 1000 g of silica (1:2:ethyl acetate:hexanes) afforded the product as a yellow foam, 9.3 g (58%).

(B)
1,2,3,4-Tetrahydro-6-methyl-4-(3-nitrophenyl)-2-thioxo-3,5-pyrimidinecarboxylic acid, 5-(1-methylethyl)ester, 3-[5(S)-methoxycarbonyl)-3(R)-pyrrolidinyl]ester 3,4-Dihydro-2-[[(4-methoxyphenyl)methyl]thio]-6-methyl-4-(3-nitrophenyl)-3,5-pyrimidinedicarboxylic acid, 5-(1-methylethyl)ester, 3-[1-[1,1-dimethylethoxy)-carbonyl]-5(S)(methoxycarbonyl)-3(R)-pyrrolidinyl ester (9.3 g, 12.8 mmol) as a solution in dichloromethane (11 ml) was added dropwise to a mixture of trifluoroacetic acid (26 ml) and anisole (2.6 ml) at 0° C. under nitrogen. The mixture was stirred at 0° C. for 90 minutes and the trifluoroacetic acid was evaporated in vacuo. The yellow residue was dissolved in dichloromethane (100 ml), and the organic layer was washed with water (50 ml), saturated sodium bicarbonate (2×50 ml), dried over magnesium sulfate, filtered and evaporated in vacuo to afford an oil. The oil was dissolved in ethyl acetate:hexanes:methanol (80:20:1), cooled to −78° C., and treated with ethereal hydrochloric acid (1 eq). The pale yellow solid was collected by filtration and dried under vacuum to afford a mixture of the diastereomers (6.0 g, 86%). The free base of the above mixture was liberated immediately prior to chromatographic separation by treating a dichloromethane solution with sodium hydroxide, and absorbing the organic layer onto Celite. Flash chromatography on 1000 g of silica using 60:40:1:ethyl acetate:hexanes:methanol, followed by an 80:20:1 ratio of the same solvent mixture afforded a separation into the two isomers A and B. All column fractions were acidified with ethereal hydrochloric acid as they were collected. Isomer A, 2.01 g (57%). Isomer B, 2.04 g (58%).

(C)
(−)-1,2,3,4-Tetrahydro-6-methyl-4-(3-nitrophenyl)-2-thioxo-5-pyrimidinecarboxylic acid, 1-methylethyl ester Sodium methoxide in methanol (2 eq.) was added to a solution of Isomer A of 1,2,3,4-tetrahydro-6-methyl-4-(3-nitrophenyl)-2-thioxo-3,5-pyrimidinecarboxylic acid, 5-(1-methylethyl)ester, 3-[(S)-5-methoxycarbonyl)-3-pyrrolidinyl]ester (2.01 g, 3.7 mmol) in methanol (4 ml). The reaction was allowed to stir at room temperature. After 16 hours, the pH was adjusted to 2 with ethereal hydrochloric acid and the mixture was cooled to −78° C. The resulting solid was collected by filtration. Three further crops were collected from the mother liquors, which when combined afforded 1.0 g (79%). $[\alpha]_D = -90.1°$ (c=1, DMSO).

(D)
(−)-1,4-Dihydro-2-[[(4-methoxyphenyl)methyl]thio]-6-methyl-4-(3-nitrophenyl)-5-pyrimidinecarboxylic acid, 1-methylethyl ester (−)-1,2,3,4-Tetrahydro-6-methyl-4-(3-nitrophenyl)-2-thioxo-5-pyrimidinecarboxylic acid, 1-methylethyl ester (2.6 mmol, 884 mg) was dissolved in dry tetrahydrofuran and cooled to 0° C. 4-Methoxybenzyl chloride (1.1 eq, 32.9 mmol, 393 μl) was added dropwise. After the addition was complete, the bath was removed and the reaction stirred at room temperature for two hours. The mixture was then heated at 65° C. for 16 hours. TLC 35:65:acetone:hexane showed an incomplete reaction, so additional 4-methoxybenzyl chloride (1.1 eq, 1.3 mmol, 393 μl) was added to the mixture. After 7 hours at 65° C., the mixture was allowed to come to room temperature and diluted with ether. As the mixture cooled to 0° C., a white solid formed. The solid was collected by suction filtration, washed with ether, and dried to afford 1,4-dihydro-2-[[(4-methoxyphenyl)methyl]thio]-6-methyl-4-(3-nitrophenyl)-5-pyrimidinecarboxylic acid, 1-methylether ester hydrochloride, 636 mg (49%).

(E)
(−)-3,4-Dihydro-3-[(dimethylamino)carbonyl]-2-[[(4-methoxyphenyl)methyl]thio]-6-methyl-4-(3-nitrophenyl)-5-pyrimidinecarboxylic acid, 1-methylethyl ester The free base of 1,4-dihydro-2-[[(4-methoxyphenyl)methyl]thio]-6-methyl-4-(3-nitrophenyl)-5-pyrimidinecarboxylic acid, 1-methylethyl ester hydrochloride was prepared by washing a dichloromethane solution with sodium bicarbonate. The organic layer was dried, filtered, and reduced in vacuo to afford a green foam. The foam (1.66 mmol, 754 mg) was dissolved in dry dichloromethane (8.3 ml) and triethylamine (5 eq, 8.3 mmol, 1.2 ml) was added. 1.3M Phosgene in toluene (1.6 eq, 2.66 mmol, 2.0 ml) was added dropwise to the mixture at 0° C. After the addition was complete, the bath was removed, and the mixture stirred at room temperature. After 30 minutes, dimethylamine (excess 1.66 ml) was added and the mixture stirred for 30 minutes. The reaction was diluted with ethyl acetate (50 ml) and washed with 1N hydrochloric acid (2×) and saturated sodium bicarbonate (2×). The organic layer was dried over magnesium sulfate, filtered, and reduced in vacuo to afford an oil, 586 mg. Flash chromatography on 40 g of silica (1:2:ethyl acetate:hexanes) afforded pure product as an oil, 355 mg (41%).

(F)
(−)-3-[(Dimethylamino)carbonyl]-1,2,3,4-tetrahydro-6-methyl-4-(3-nitrophenyl)-2-oxo-5-pyrimidinecarboxylic acid, 1-methylethyl ester 3-Chloroperoxybenzoic acid (3 eq, 2.0 mmol, 349 mg) was added to a solution of (−)-3,4-dihydro-3-[(dimethylamino)carbonyl]-2-[[(4-methoxyphenyl)methyl]thio]-6-methyl-4-(3-nitrophenyl)-5-pyrimidinecarboxylic acid, 1-methylethyl ester in dry dichloromethane (6.7 ml) at 0° C. under a nitrogen atmosphere. The reaction was stirred overnight at room temperature, and a precipitate formed. The mixture was diluted with ethyl acetate (15 ml) and washed with 1N hydrochloric acid (twice), 1N sodium hydroxide (twice) and water. The combined organic layers were dried over magnesium sulfate, filtered, and reduced in vacuo to afford an oil, 390 mg. Flash chromatography on 39 g silica gel (2:1:ethyl acetate:hexanes) afforded the product as an oil. The oil was allowed to stand under ether for a 48 hour period, and was then triturated to produce a white crystalline solid, 144 mg (55%), melting point 152°–153° C. $[\alpha]_D = -128.6°$ (c=1.2, chloroform).

Analysis Calc'd. for $C_{18}H_{22}N_4O_6$: C, 55.38; H, 5.68; N, 14.35. Found: C, 55.41; H, 5.68; N, 14.17

EXAMPLE 21

(+)-3-[(Dimethylamino)carbonyl]-1,2,3,4-tetrahydro-6-methyl-4-(3-nitrophenyl)-2-oxo-5-pyrimidinecarboxylic acid, 1-methylethyl ester (A)

(+)-1,2,3,4-Tetrahydro-6-methyl-4-(3-nitrophenyl)-2-thioxo-5-pyrimidinecarboxylic acid, 1-methylethyl ester Sodium methoxide in methanol (1.6 ml, 7.5 mmol, 2 eq) was added to a solution of isomer B [described in Example 20, part B] of 1,2,3,4-tetrahydro-6-methyl-4-(3-nitrophenyl)-2-thioxo-3,5-pyrimidinecarboxylic acid, 5-(1-methylethyl)ester, 3-[(S)-5-methoxycarbonyl)-3-pyrrolidinyl]ester (2.04 g, 3.7 mmol) in methanol (18 ml). The reaction was allowed to stir at room temperature. After 16 hours, the pH was adjusted to 2 with ethereal hydrochloric acid and the mixture was cooled to 0° C. for six hours. The resulting solid was collected by filtration. Three further crops were collected from the mother liquors, which when combined afforded 1.12 g (89%). $[\alpha]_D = +85°$ (c=0.5, dimethylsulfoxide).

(B)

(+)-1,4-Dihydro-2-[[(4-methoxyphenyl)methyl]thio]-6-methyl-4-(3-nitrophenyl)-5-pyrimidinecarboxylic acid, 1-methylethyl ester (+)-1,2,3,4-Tetrahydro-6-methyl-4-(3-nitrophenyl)-2-thioxo-5-pyrimidinecarboxylic acid, 1-methylethyl ester (2.6 mmol, 884 mg) was dissolved in dry tetrahydrofuran and cooled to 0° C. 4-Methoxybenzyl chloride (1.1 eq, 32.9 mmol, 393 μl) was added dropwise. After the addition was complete, the bath was removed and the reaction stirred at room temperature for two hours. The mixture was then heated at 65° C. for 16 hours. TLC 35:65:acetone:hexane showed an incomplete reaction, so additional 4-methoxybenzyl chloride (0.5 eq, 1.3 mmol, 176 μl) was added to the mixture. After seven hours at 65° C., the mixture was allowed to come to room temperature and diluted with ether. As the mixture cooled to 0° C., a white solid formed. The solid was collected by suction filtration, washed with ether, and dried to afford (+)-1,4-dihydro-2-[[(4-methoxyphenyl)methyl]thio]-6-methyl-4-(3-nitrophenyl)-5-pyrimidinecarboxylic acid, 1-methylethyl ester hydrochloride, 493 mg (38%).

(C)

(+)-3,4-Dihydro-3-[(dimethylamino)carbonyl]-2-[[(4-methoxyphenyl)methyl]thio]-6-methyl-4-(3-nitrophenyl)-5-pyrimidinecarboxylic acid, 1-methylethyl ester The free base of (+)-1,4-dihydro-2-[[(4-methoxyphenyl)methyl]thio]-6-methyl-4-(3-nitrophenyl)-5-pyrimidinecarboxylic acid, 1-methylethyl ester hydrochloride was prepared by washing a dichloromethane solution with sodium bicarbonate. The organic layer was dried, filtered, and reduced in vacuo to afford a green foam. The foam (0.95 mmol, 431 mg) was dissolved in dry dichloromethane (4.8 ml) and triethylamine (5 eq, 4.75 mmol) was added. 1.3M Phosgene in toluene (1.6 eq, 1.5 mmol, 662 μl) was added dropwise to the mixture at 0° C. After the addition was complete, the bath was removed, and the mixture stirred at room temperature. After 30 minutes, dimethylamine (excess, 0.95 ml) was added and the mixture stirred for 30 minutes. The reaction was diluted with ethyl acetate (50 ml) and washed with 1N hydrochloric acid (twice) and saturated sodium bicarbonate (twice). The organic layer was dried over magnesium sulfate, filtered and reduced in vacuo to afford an oil. Flash chromatography on 40 g silica (1:2:ethyl acetate:hexanes), afforded pure product as an oil, 431 mg (86%).

(D)

(+)-3-[(Dimethylamino)carbonyl]-1,2,3,4-tetrahydro-6-methyl-4-(3-nitrophenyl)-2-oxo-5-pyrimidinecarboxylic acid, 1-methylethyl ester 3-Chloroperoxybenzoic acid (3 eq, 2.5 mmol, 424 mg) was added to a solution of (+)-3,4-dihydro-3-[(dimethylamino)carbonyl]-2-[[(4-methoxyphenyl)methyl]thio]-6-methyl-4-(3-nitrophenyl)-5-pyrimidinecarboxylic acid, 1-methylethyl ester in dry dichloromethane (8.2 ml) at 0° C. under a nitrogen atmosphere. The reaction was stirred overnight at room temperature, and a precipitate formed. The mixture was diluted with ethyl acetate (15 ml) and washed with 1N hydrochloric acid (twice), 1N sodium hydroxide (twice) and water. The combined organic layers were dried over magnesium sulfate, filtered, and reduced in vacuo to afford an oil, 390 mg.

Flash chromatography on 39 g silica gel (2:1:ethyl acetate:hexanes) afforded the product as an oil (433 mg). The oil was allowed to stand under ether for a 48 hour period, and was then triturated to produce a white crystalline solid, 254 mg (67%), melting point 153°–155° C. $[\alpha]_D = +112.5°$ (c=1.1, chloroform).

Analysis Calc'd. for $C_{18}H_{22}N_4O_6$: C, 55.38; H, 5.68; N, 14.35. Found: C, 55.32; H, 5.76; N, 14.00

EXAMPLE 22

3-(Aminocarbonyl)-1,2,3,4-tetrahydro-6-methyl-4-(3-nitrophenyl)-2-oxo-5-pyrimidinecarboxylic acid, 1-methylethyl ester, (+)-isomer The solution of [3(S)]-1,2,3,4-tetrahydro-6-methyl-4-(3-nitrophenyl)-2-oxo-3-[[(1-phenylethyl)amino]carbonyl]-5-pyrimidinecarboxylic acid, 1-methylethyl ester, isomer B (1.7 g, 3.65 mmol; as in Example 14) in trifluoroacetic acid (10 ml) was heated at 75° C. for 4 hours. The reaction was allowed to cool down to room temperature and the solvent was evaporated. The residue was dissolved in ethyl acetate and was washed with water, sodium bicarbonate and brine. It was dried over magnesium sulfate and evaporated to yield a yellow foam. Crystallization from isopropyl ether-ether provided a colorless solid (1.12 g). Recrystallization from isopropyl ether-dichloromethane provided the analytically pure 3-(aminocarbonyl)-1,2,3,4-tetrahydro-6-methyl-4-(3-nitrophenyl)-2-oxo-5-pyrimidinecarboxylic acid, 1-methylethyl ester, (+)-isomer (870 mg), melting point 160°–161° C., $[\alpha]_D = +153°$ (1% in methanol).

Analysis Calc'd. for $C_{16}H_{18}N_4O_6$: C, 53.03; H, 5.01; N, 15.47. Found: C, 53.06; H, 5.01; N, 15.47

EXAMPLE 23

3-(Aminocarbonyl)-1,2,3,4-tetrahydro-6-methyl-4-(3-nitrophenyl)-2-oxo-5-pyrimidinecarboxylic acid, 1-methylethyl ester, (−)-isomer The solution of [3(S)]-1,2,3,4-tetrahydro-6-methyl-4-(3-nitrophenyl)-2-oxo-3-[[(1-phenylethyl)amino]carbonyl]-5-pyrimidinecarboxylic acid, 1-methylethyl ester, isomer A (60 mg, 0.13 mmol; as in Example 14) in trifluoroacetic acid (10 ml) was heated at 75° C. for 4 hours. The reaction was allowed to cool down to room temperature and the solvent was evaporated. The residue was dissolved in ethyl acetate and was washed with water, sodium bicarbonate and brine. It was dried over magnesium sulfate and evaporated to yield a yellow foam. Crystallization from isopropyl ether-dichloromethane provided 3-(aminocarbonyl)-1,2,3,4-tetrahydro-6-methyl-4-(3-nitrophenyl)-2-oxo-5-pyrimidinecarboxylic acid, 1-methylethyl ester, (−)-isomer (27 mg), melting point 160°–161° C., $[\alpha]_D = -149°$ (1% in methanol).

Analysis Calc'd. for $C_{16}H_{18}N_4O_6$: C, 53.03; H, 5.01; N, 15.47. Found: C, 53.20; H, 5.12; N, 15.11

Additional compounds falling within the scope of this invention are:

4-(2,3-dichlorophenyl)-1,2,3,4-tetrahydro-6-methyl-3-[[(methyl)(phenylmethyl)amino]carbonyl]-2-oxo-5-pyrimidinecarboxylic acid, ethyl ester 1,2,3,4-tetrahydro-6-methyl-4-(2-nitrophenyl)-2-oxo-3-[[(4-phenylmethyl)-1-piperazinyl]carbonyl]-5-pyrimidinecarboxylic acid, ethyl ester 1,2,3,4-tetrahydro-6-methyl-3-(N-morpholinylcarbonyl)-4-(3-nitrophenyl)-2-oxo-5-pyrimidinecarboxylic acid, 2-[(methyl)(phenylmethyl)amino]ethyl ester 4-(7-benzofurazanyl)-1,2,3,4-tetrahydro-6-methyl-2-oxo-3-[[4-(diphenylmethyl)-1-piperazinyl]carbonyl]-5-pyrimidinecarboxylic acid, ethyl ester 1,2,3,4-tetrahydro-6-methyl-4-[2-(methylthio)-3-pyridinyl]-3-[[[(methyl)[2-[(methyl)(phenylmethyl)amino]ethyl]]amino]carbonyl]-2-oxo-5-pyrimidinecarboxylic acid, ethyl ester 3-[[(cyclohexyl)(methyl)amino]carbonyl]-1,2,3,4-tetrahydro-6-methyl-2-oxo-4-[2-(trifluoromethyl)phenyl]-5-pyrimidinecarboxylic acid, ethyl ester 1,2,3,4-tetrahydro-6-methyl-3-[[(methyl)(phenyl)amino]carbonyl]-4-(3-nitrophenyl)-2-oxo-5-pyrimidinecarboxylic acid, 1-(phenylmethyl)-4-piperidinyl ester 4-(2-chloro-3-nitrophenyl)-1,2,3,4-tetrahydro-6-methyl-3-[[(methyl)(1-methylethyl)amino]carbonyl]-2-oxo-5-pyrimidinecarboxylic acid, 1-diphenylmethyl-4-piperidinyl ester 4-(2,3-dichlorophenyl)-1,2,3,4-tetrahydro-6-methyl-3-[[(methyl)(phenylmethyl)amino]carbonyl]-2-thioxo-5-pyrimidinecarboxylic acid, ethyl ester 1,2,3,4-tetrahydro-6-methyl-4-(3-nitrophenyl)-3-(1-piperidinylcarbonyl)-2-thioxo-5-pyrimidinecarboxylic acid, 1-methylethyl ester 1,2,3,4-tetrahydro-6-methyl-4-(2-nitrophenyl)-3-[[(4-phenylmethyl)-1-piperazinyl]carbonyl]-2-thioxo-5-pyrimidinecarboxylic acid, ethyl ester 1,2,3,4-tetrahydro-6-methyl-3-(N-morpholinylcarbonyl)-4-(3-nitrophenyl)-2-thioxo-5-pyrimidinecarboxylic acid, 2-[(methyl)(phenylmethyl)amino]ethyl ester 4-(7-benzofurazanyl)-1,2,3,4-tetrahydro-6-methyl-3-[[(4-(diphenylmethyl)-1-piperazinyl]carbonyl]-2-thioxo-5-pyrimidinecarboxylic acid, ethyl ester 1,2,3,4-tetrahydro-6-methyl-4-[2-(methylthio)-3-pyridinyl]-3-[[[(methyl)[2-[(methyl)(phenylmethyl)amino]ethyl]]amino]carbonyl]-2-thioxo-5-pyrimidinecarboxylic acid, ethyl ester 3-[[(cyclohexyl)(methyl)amino]carbonyl]-1,2,3,4-tetrahydro-6-methyl-2-thioxo-4-[2-(trifluoromethyl)phenyl]-5-pyrimidinecarboxylic acid, ethyl ester 1,2,3,4-tetrahydro-6-methyl-3-[[(methyl)(phenyl)amino]carbonyl]-4-(3-nitrophenyl)-2-thioxo-5-pyrimidinecarboxylic acid, 1-(phenylmethyl)-4-piperidinyl ester 1-(2-chloro-3-nitrophenyl)-1,2,3,4-tetrahydro-6-methyl-3-[[(methyl)(1-methylethyl)amino]carbonyl]-2-thioxo-5-pyrimidinecarboxylic acid, 1-diphenylmethyl-4-piperidinyl ester

What is claimed is:

1. A compound having the formula

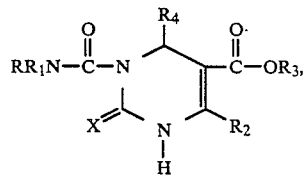

or a pharmaceutically acceptable salt thereof wherein
X is oxygen or sulfur;
R is hydrogen, alkyl, cycloalkyl, aryl, or arylalkyl and $R_1$ is hydrogen, alkyl, cycloalkyl, aryl,

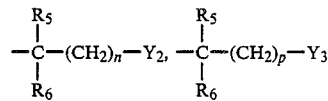

or halo substituted alkyl, or R and $R_1$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl or 1-pyrrolidinyl, 1-piperidinyl, or 1-azepinyl substituted with alkyl, alkoxy, alkylthio, halo, trifluoromethyl or hydroxy;

$R_2$ is hydrogen, alkyl, alkenyl, alkynyl, cycloalkyl, aryl,

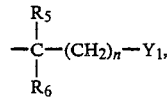

or halo substituted alkyl;

$R_3$ is hydrogen, alkyl, cycloalkyl, aryl,

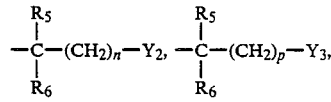

or halo substituted alkyl;

$R_4$ is 2,1,3-benzoxadiazol-4-yl, phenyl, or phenyl substituted with one, two or three alkyl, halo, nitro, cyano, amino, dialkylamino, trifluoromethyl, isothiocyanato or isocyanato groups;

$R_5$ and $R_6$ are each independently hydrogen, alkyl, —$(CH_2)_q$—aryl or —$(CH_2)_q$—cycloalkyl;

$Y_1$ is cycloalkyl, aryl, hydroxyl, alkoxy, aryl—$(CH_2)_m$—O—, mercapto, alkylthio, aryl—$(CH_2)_m$—S—, amino, substituted amino, carbamoyl,

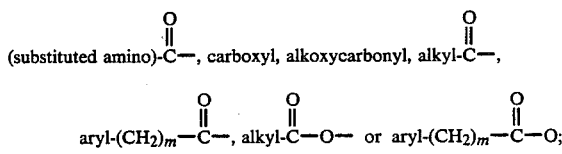

$Y_2$ is cycloalkyl, aryl, carbamoyl,

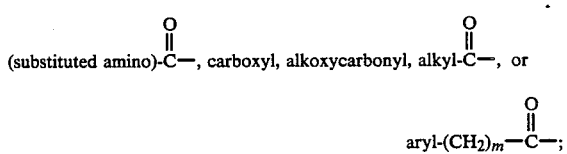

$Y_3$ is hydroxyl, alkoxy, aryl—$(CH_2)_m$—O—, mercapto, alkylthio, aryl—$(CH_2)_m$—S—,

amino, or substituted amino;
q is 0, 1, 2 or 3;
m is 0 or an integer of 1 to 6;
n is 0 or an integer of 1 to 5; and
p is an integer of 1 to 5; wherein
the term "cycloalkyl" refers to a cycloalkyl group having 3, 4, 5, 6 or 7 carbon atoms;
the term "aryl" refers to phenyl or phenyl substituted with one, two or three alkyl, alkoxy, alkylthio, halo, nitro, cyano, hydroxy, amino, alkylamino, dialkylamino, trifluoromethyl, isothiocyanato, isocyanato, or difluoromethoxy groups;
the term "substituted amino" refers to a group of the formula —$NZ_1Z_2$ wherein $Z_1$ is hydrogen, alkyl, or aryl—$(CH_2)_m$— and $Z_2$ is alkyl or aryl—$(CH_2)_m$—.

2. A compound in accordance with claim 1 wherein $R_4$ is phenyl or phenyl substituted with one, two or three alkyl, halo, nitro, cyano, amino, dialkylamino, trifluoromethyl, isothiocyanato or isocyanato groups.

3. A compound in accordance with claim 2 wherein X is oxygen.

4. A compound in accordance with claim 2 wherein X is sulfur.

5. A compound in accordance with claim 3 wherein $R_2$ is alkyl.

6. A compound in accordance with claim 4 wherein $R_2$ is alkyl.

7. A compound in accordance with claim 3 wherein $R_3$ is alkyl.

8. A compound in accordance with claim 4 wherein $R_3$ is alkyl.

9. A compound in accordance with claim 3 wherein $R_4$ is 3-nitrophenyl.

10. A compound in accordance with claim 4 wherein $R_4$ is 3-nitrophenyl.

11. A compound in accordance with claim 1 wherein $R_4$ is 2,1,3-benzoxadiazol-4-yl.

12. A compound in accordance with claim 2 wherein R is hydrogen, alkyl, aryl, or arylalkyl and $R_1$ is alkyl, aryl or arylalkyl.

13. A compound in accordance with claim 2 wherein R and $R_1$ taken together with the nitrogen atom to which they are attached are 1-pyrrolidinyl, 1-piperidinyl, 1-azepinyl, 4-morpholinyl, 4-thiamorpholinyl, 1-piperzinyl, 4-alkyl-1-piperazinyl, 4-arylalkyl-1-piperazinyl, 4-diarylalkyl-1-piperazinyl or 1-pyrrolidinyl, 1-piperidinyl, or 1-azeipinyl substituted with alkyl, alkoxy, alkylthio, halo, trifluoromethyl or hydroxy.

14. A compound in accordance with claim 2 wherein R and $R_1$ are each alkyl.

15. A compound in accordance with claim 2 wherein X is sulfur, $R_2$ is methyl, $R_3$ is ethyl and $R_4$ is 3-nitrophenyl.

16. The compound in accordance with claim 1, 3-[(ethylamino)carbonyl]-1,2,3,4-tetrahydro-6-methyl-4-(3-nitrophenyl)-2-thioxo-5-pyrimidinecarboxylic acid, methyl ester.

17. The compound in accordance with claim 1, 3-[(dimethylamino)carbonyl]-1,2,3,4-tetrahydro-6-methyl-4-(3-nitrophenyl)-2-oxo-5-pyrimidinecarboxylic acid, 1-methylethyl ester.

18. The compound in accordance with claim 1, 3-[(dimethylamino)carbonyl]-1,2,3,4-tetrahydro-6-methyl-4-(3-nitrophenyl)-2-thioxo-5-pyrimidinecarboxylic acid, ethyl ester.

19. The compound in accordance with claim 1, 3-(aminocarbonyl)-1,2,3,4-tetrahydro-6-methyl-4-(3-nitrophenyl)-2-oxo-5-pyrimidinecarboxylic acid, 1-methylethyl ester.

20. The compound in accordance with claim 1, [3(S)]-1,2,3,4-tetrahydro-6-methyl-4-(3-nitrophenyl)-2-oxo-3-[[(1-phenylethyl)amino]carbonyl]-5-pyrimidinecarboxylic acid, 1-methylethyl ester.

21. The compound in accordance with claim 1, 1,2,3,4-tetrahydro-6-methyl-3-[[[2-[methyl(phenylmethyl)amino]ethyl]amino]carbonyl]-4-(3-nitrophenyl)-2-oxo-5-pyrimidinecarboxylic acid, 1-methylethyl ester.

22. The nonracemic form of the compound of claim 19 having a negative optical rotation.

23. A method of treating a disease susceptible to treatment by a calcium entry blocking vasodilator in a mammalian host in need thereof, which comprises administering to said host a compound having the formula

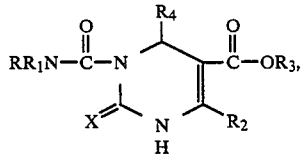

or a pharmaceutically acceptable salt thereof in an amount which is effective for the treatment of a disease susceptible to treatment by a calcium entry blocking vasodilator, wherein
X is oxygen or sulfur;
R is hydrogen, alkyl, cycloalkyl, aryl, or arylalkyl and $R_1$ is hydrogen, alkyl, cycloalkyl, aryl,

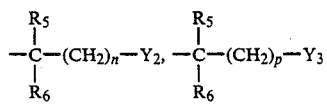

or halo substituted alkyl, or R and R₁ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl or 1-pyrrolidinyl, 1-piperidinyl, or 1-azepinyl substituted with alkyl, alkoxy, alkylthio, halo, trifluoromethyl or hydroxy;

R₂ is hydrogen, alkyl, alkenyl, alkynyl, cycloalkyl, aryl,

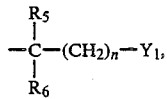

or halo substituted alkyl;
R₃ is hydrogen, alkyl, cycloalkyl, aryl,

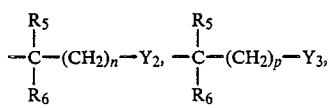

or halo substituted alkyl;
R₄ is aryl or 2,1,3-benzoxadiazol-4-yl;
R₅ and R₆ are each independently hydrogen, alkyl, —(CH₂)_q—aryl or —(CH₂)_q—cycloalkyl;
Y₁ is cycloalkyl, aryl, hydroxyl, alkoxy, aryl—(CH₂)_m—O—, mercapto, alkylthio, aryl—(CH₂)_m—S—, amino, substituted amino, carbamoyl,

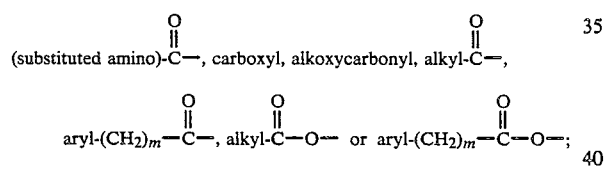

Y₂ is cycloalkyl, aryl, carbamoyl,

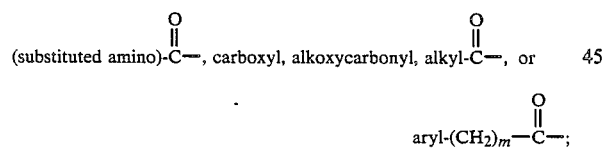

Y₃ is hydroxyl, alkoxy, aryl—(CH₂)_m—O—, mercapto, alkylthio, aryl—(CH₂)_m—S—,

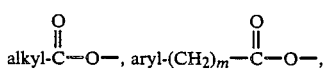

amino, or substituted amino;
q is 0, 1, 2 or 3;
m is 0 or an integer of 1 to 6;
n is 0 or an integer of 1 to 5; and
p is an integer of 1 to 5; wherein
the term "cycloalkyl" refers to a cycloalkyl group having 3, 4, 5, 6 or 7 carbon atoms;
the term "aryl" refers to phenyl or phenyl substituted with one, two or three alkyl, alkoxy, alkylthio, halo, nitro, cyano, hydroxy, amino, alkylamino, dialkylamino, trifluoromethyl, isothiocyanato, isocyanato, or difluoromethoxy groups;

the term "substituted amino" refers to a group of the formula —NZ₁Z₂ wherein Z₁ is hydrogen, alkyl, or aryl—(CH₂)_m— and Z₂ is alkyl or aryl—(CH₂)_m—.

24. A method in accordance with claim 23 wherein R₄ is aryl.

25. A pharmaceutical composition useful for the treatment of a disease susceptible to treatment by a calcium entry blocking vasodilator comprising a compound having the formula

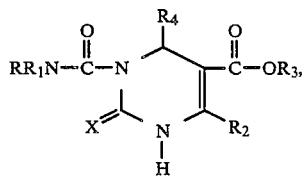

or a pharmaceutically acceptable salt thereof in an amount which is effective for the treatment of a disease susceptible to treatment by a calcium entry blocking vasodilator, wherein
X is oxygen or sulfur;
R is hydrogen, alkyl, cycloalkyl, aryl, or arylalkyl and R₁ is hydrogen, alkyl, cycloalkyl, aryl

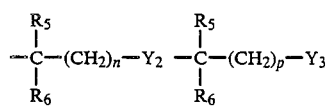

or halo substituted alkyl, or R and R₁ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl or 1-pyrrolidinyl, 1-piperidinyl, or 1-azepinyl substituted with alkyl, alkoxy, alkylthio, halo, trifluoromethyl or hydroxy;

R₂ is hydrogen, alkyl, alkenyl, alkynyl, cycloalkyl, aryl

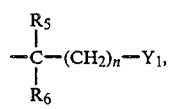

or halo substituted alkyl;
R₃ is hydrogen, alkyl, cycloalkyl, aryl,

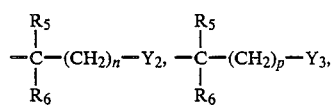

or halo substituted alkyl;
R₄ is aryl or 2,1,3-benzoxadiazol-4-yl;
R₅ and R₆ are each independently hydrogen, alkyl, —(CH₂)_q—aryl or —(CH₂)_q—cycloalkyl;
Y₁ is cycloalkyl, aryl, hydroxyl, alkoxy, aryl—(CH₂)_m—O—, mercapto, alkylthio, aryl—(CH₂)_m—S—, amino, substituted amino, carbamoyl,

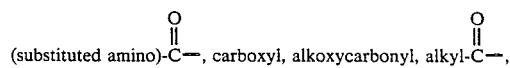

-continued $$\text{aryl-}(CH_2)_m-\overset{O}{\underset{\|}{C}}-,\ \text{alkyl-}\overset{O}{\underset{\|}{C}}-O-\ \text{or aryl-}(CH_2)_m-\overset{O}{\underset{\|}{C}}-O-;$$

Y$_2$ is cycloalkyl, aryl, carbamoyl, $$\text{(substituted amino)-}\overset{O}{\underset{\|}{C}}-,\ \text{carboxyl, alkoxycarbonyl, alkyl-}\overset{O}{\underset{\|}{C}}-,\ \text{or}$$

$$\text{aryl-}(CH_2)_m-\overset{O}{\underset{\|}{C}}-;$$

Y$_3$ is hydroxyl, alkoxy, aryl—(CH$_2$)$_m$—O—, mercapto, alkylthio, aryl—(CH$_2$)$_m$—S—, $$\text{alkyl-}\overset{O}{\underset{\|}{C}}-O-,\ \text{aryl-}(CH_2)_m-\overset{O}{\underset{\|}{C}}-O-,$$

amino, or substituted amino;
q is 0, 1, 2 or 3;
m is 0 or an integer of 1 to 6;
n is 0 or an integer of 1 to 5; and
p is an integer of 1 to 5,
and a pharmaceutically acceptable carrier therefore;
wherein
  the term "cycloalkyl" refers to a cycloalkyl group having 3, 4, 5, 6 or 7 carbon atoms;
  the term "aryl" refers to phenyl or phenyl substituted with one, two or three alkyl, alkoxy, alkylthio, halo, nitro, cyano, hydroxy, amino, alkylamino, dialkylamino, trifluoromethyl, isothiocyanato, isocyanato, or difluoromethoxy groups;
  the term "substituted amino" refers to a group of the formula —NZ$_1$Z$_2$ wherein Z$_1$ is hydrogen, alkyl, or aryl—(CH$_2$)$_m$— and Z$_2$ is alkyl or aryl—(CH$_2$)$_m$—.

26. A pharmaceutical composition in accordance with claim 25 wherein R$_4$ is aryl.

* * * * *